United States Patent
Hammer

(10) Patent No.: US 12,303,645 B2
(45) Date of Patent: May 20, 2025

(54) HEADGEAR FOR A PATIENT INTERFACE

(71) Applicant: Fisher & Paykel Healthcare Limited, Auckland (NZ)

(72) Inventor: Jeroen Hammer, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 934 days.

(21) Appl. No.: 17/434,369

(22) PCT Filed: Feb. 24, 2020

(86) PCT No.: PCT/IB2020/051507
§ 371 (c)(1),
(2) Date: Aug. 26, 2021

(87) PCT Pub. No.: WO2020/174344
PCT Pub. Date: Sep. 3, 2020

(65) Prior Publication Data
US 2022/0088340 A1   Mar. 24, 2022

Related U.S. Application Data

(60) Provisional application No. 62/811,754, filed on Feb. 28, 2019.

(51) Int. Cl.
*A61M 16/06* (2006.01)

(52) U.S. Cl.
CPC . *A61M 16/0683* (2013.01); *A61M 2205/0216* (2013.01)

(58) Field of Classification Search
CPC .......... A62B 18/084; A42B 1/22; A42B 1/24; A42B 3/324
See application file for complete search history.

(56) References Cited

U.S. PATENT DOCUMENTS

| | | | |
|---|---|---|---|
| 5,238,278 A * | 8/1993 | Kamper | B66C 1/18 139/408 |
| 2015/0028519 A1* | 1/2015 | Lang | A61M 16/0633 264/255 |
| 2016/0166793 A1 | 6/2016 | McLaren et al. | |
| 2018/0214656 A1* | 8/2018 | McLaren | A61M 16/16 |

FOREIGN PATENT DOCUMENTS

| WO | WO-2013026091 A1 * | 2/2013 | A61M 16/06 |
|---|---|---|---|
| WO | WO 2019/003094 | 1/2019 | |

OTHER PUBLICATIONS

International Search Report for PCT Application No. PCT/IB2020/051507 dated Jul. 15, 2020.
Written Opinion for PCT Application No. PCT/IB2020/051507 dated Jul. 15, 2020.

* cited by examiner

Primary Examiner — Kendra D Carter
Assistant Examiner — Jaeick Jang
(74) Attorney, Agent, or Firm — VIA LLP

(57) ABSTRACT

Headgear for a respiratory interface has a strap assembly with an elongate flexible strap, a rail extending longitudinally along a rail portion of the strap, and a slide member having a channel that receives the rail. The slide member is attached to an attachment portion of the flexible strap and slidable along the rail to adjust the length of the strap assembly.

15 Claims, 18 Drawing Sheets

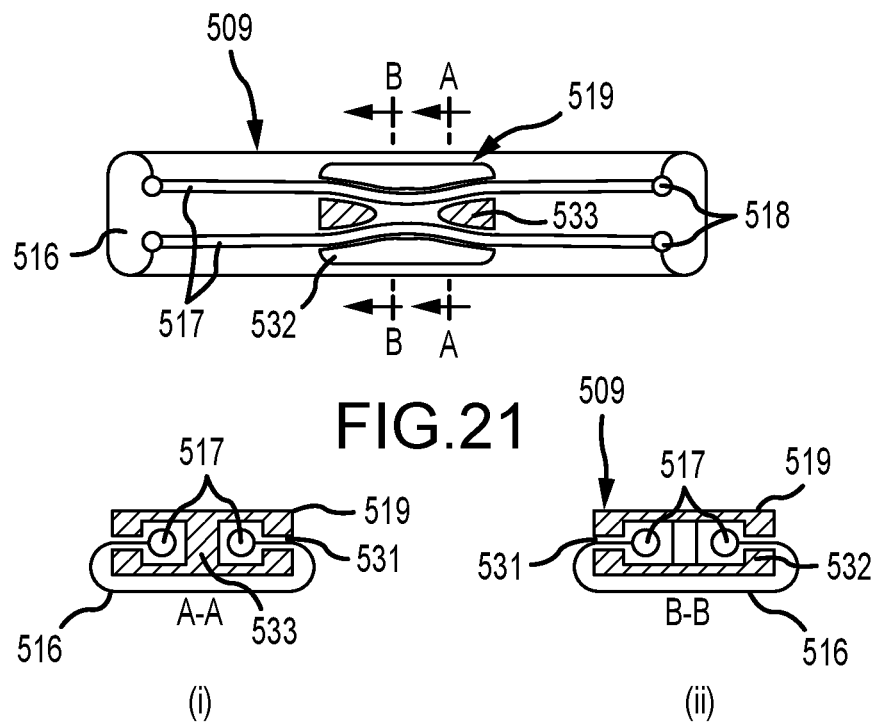
FIG.21
FIG.22
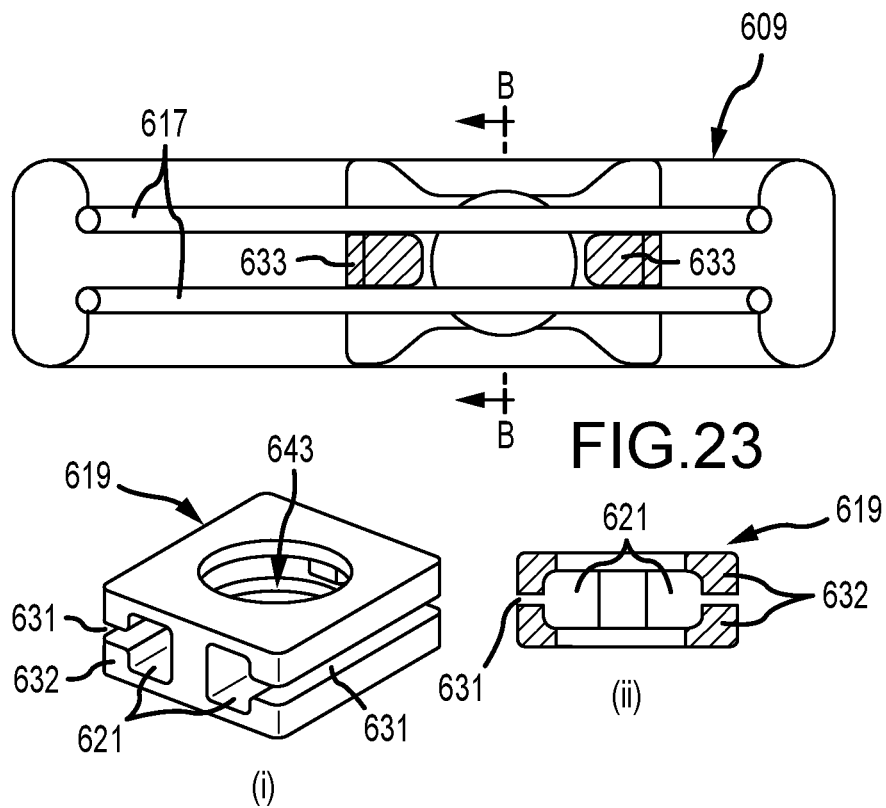
FIG.23
FIG.24

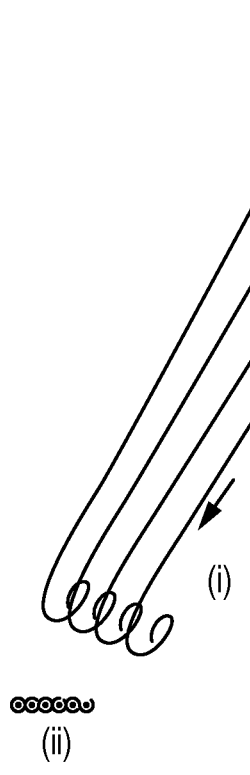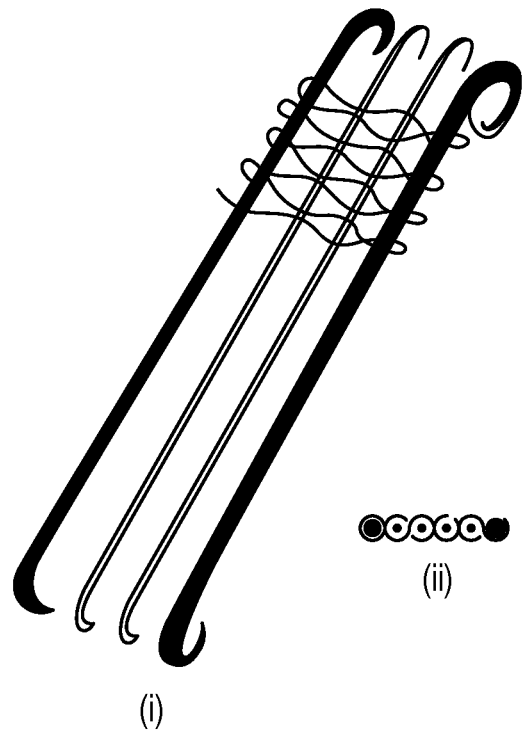
FIG.38　　　FIG.39
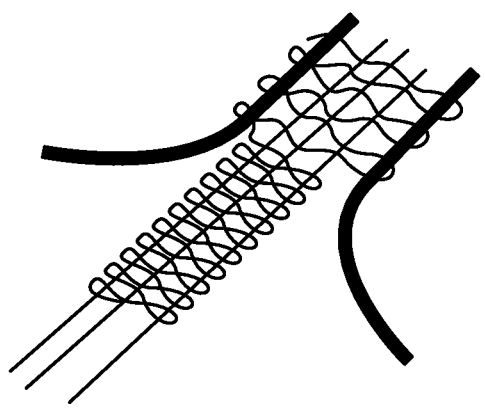
FIG.40

HEADGEAR FOR A PATIENT INTERFACE

FIELD OF THE INVENTION

The present disclosure generally relates to headgear for a patient interface, in particular to a strap assembly with a slide member for adjusting headgear for a respiratory patient interface.

BACKGROUND

Patient interfaces are used to provide respiratory therapy to the airways of a person suffering from any of a number of respiratory illnesses or conditions. Such therapies may include but are not limited to continuous positive airway pressure (CPAP) therapy and non-invasive ventilation (NIV) therapy.

CPAP therapy can be used to treat obstructive sleep apnoea (OSA), a condition in which a patient's airway intermittently collapses during sleep, preventing the patient from breathing for a period of time. The cessation of breathing, or apnoea, results in the patient awakening. Repetitive and frequent apnoeas may result in the patient rarely achieving a full and restorative night's sleep.

CPAP therapy involves the delivery of a supply of continuous positive air pressure to the airway of the patient via a patient interface. The continuous positive pressure acts to keep the airway in an open position so the patient's breathing and sleep are not interrupted.

CPAP therapy requires the user to wear a respiratory interface which seals against a user's face, around their nose and/or mouth via a seal/cushion to deliver respiratory gas or gases such as air to a user under positive pressure. Such patient interfaces may also be used to deliver NIV and other therapies.

Patient interfaces are available in a range of styles including full-face, nasal, direct nasal and oral masks. The seal/cushion is held in place against the user's face by headgear. The headgear provides support to the respiratory interface such that it is held in a stable position relative to the user's face during use. Because of the wide variation in size and shape of individuals' heads, it is desirable for the headgear to be adjustable so it can be adjusted to fit each user. It is desirable for any adjustment to be fine or substantially continuous rather than stepwise to ensure the headgear can be fitted well to a wide range of individuals.

Some existing adjustable straps, such as those using hook-and-loop fasteners, rely on the wearer disconnecting one end of the strap, adjusting the strap, and aligning and reattaching the strap end. Attaching and correctly aligning such fasteners can be difficult for a wearer, particularly because the adjusters are usually located in a region that is not visible, such as the sides of rear of the head. Incorrect alignment can result in a poor seal between the patient interface and the patient, compromising CPAP therapy. Further, performing fine motor tasks in this region can be difficult for some individuals. If the individual loses grip of the strap end or does not fully re-attach the strap, the strap may unthread from its attachment to the respiratory interface resulting in the interface coming loose.

Patients may be deterred from using CPAP therapy if they find the respiratory interface or accompanying headgear uncomfortable or invasive. During the treatment of OSA, a patient wears the interface while they sleep, so the interface and headwear must be comfortable and not cause irritation, and the mask and headgear must fit with enough stability to not be dislodged as the patient turns in their sleep.

In this specification where reference has been made to patent specifications, other external documents, or other sources of information, this is generally to provide a context for discussing features of the invention. Unless specifically stated otherwise, reference to such external documents or sources of information is not to be construed as an admission that such documents or such sources of information, in any jurisdiction, are prior art or form part of the common general knowledge in the art.

SUMMARY OF THE INVENTION

In a first aspect, the present disclosure relates to headgear for a respiratory interface having a strap assembly. The strap assembly comprises an elongate flexible strap, a rail extending longitudinally along a rail portion of the strap, and a slide member having a channel that receives the rail. The slide member is attached to an attachment portion of the flexible strap and slidable along the rail to adjust the length of the strap assembly. The strap comprises woven threads of different thicknesses, or woven bundles of varying numbers of threads to vary the width or thickness of the strap.

In an embodiment, the slide member is fixedly attached to the attachment portion of the flexible strap.

The slide member is fixedly attached such that the attached portion of the strap and the slide member are in a fixed arrangement with respect to each other when attached together. In other words, there is no relative movement between the attached portion of strap and the slide member when they are fixedly attached to each other.

In an embodiment, the rail is formed from a portion of the strap that is folded or looped on itself to create a longitudinal thickened region or longitudinal protrusion. The rail may attach to the strap via an adjoining web. The rail may comprise a cord or bundle of fibres, which may be attached to the strap by stitching the cord directly to the strap or the strap may be wrapped over cord and stitched along a stitch line parallel to the cord. The rail may comprise an enlarged portion of the strap. For example, the rail may comprise a longitudinal protrusion that is integrally formed by knitting or weaving the strap with a thicker portion of the strap. The rail may comprise a plastic material such as silicone, TPU or TPE that has been overmoulded to the strap. The overmoulded rail may have a greater cross-sectional area than the strap. The overmoulded rail may comprise a plurality of segments that are spaced apart along an edge of the strap. By providing the rail as a plurality of segments, a more rigid material may be used for the rail whilst maintaining sufficient flexibility in the strap.

In an embodiment, the rail is substantially aligned with a centre line of the strap rail portion. The strap assembly may comprise a single rail or may comprise a plurality of rails, for example two, three, four, or more rails.

Some embodiments comprise a pair of rails, each rail being provided along an opposite side edge of the strap. In such embodiments, the slide member comprises two corresponding channels to receive the two rails. The rail portion of the strap may form a C-shape cross section, at least in a region adjacent the slide member, with the channels in the slide member opening to the sides of the slide member to receive the webs of the rails.

In an embodiment, the, or each, rail has a width that is greater than a thickness of the strap or web adjacent the rail.

The rail may have a lead-in portion at one end or both ends to facilitate assembly of the slide member onto the rail.

The lead-in portion may comprise a tapered, sloped, or thinned section of web and/or rail to guide the slide member onto the rail.

The slide member may be attached to the flexible strap at or near a free end of the strap. This attachment may be permanent, for example using an adhesive or over moulding, or removable using hook-and-loop type fasteners, buttons, or other suitable removable attachments.

In an embodiment, the or each slide member channel comprises a profile having a main recess to receive the rail and a necked opening to receive the strap or web extending between the rail and the strap. An underside of the slide member may slide over and bear against the strap along the rail portion.

The opening may comprise an open-ended slot on the bottom or a side surface of the slide member. The opening has a width that is narrower than the width of the main recess. For example, each channel may be keyhole-type slot, for example with an omega (Ω) shaped profile. This narrowed opening retains the rail in the slot to reduce the likelihood of inadvertent derailing of the slide member from the rail.

In an embodiment, the channel opening has a width equal to or larger than a thickness of the web or the portion of the strap adjoining the rail, thereby allowing the passage of the web or said strap portion through the opening.

The rail portion may comprise a stop at least one end of the rail portion to limit movement of the slide member along the rail. The stop may be provided by a protrusion, an enlarged portion of rail or web, or by an attachment point joining the rail to an adjacent portion of strap such as may be provided by stitching the rail to the strap or by flattening the rail at an attachment to an adjoining piece of the headgear, for example to the rear head receiving portion of the headgear.

Friction forces act between the slide member and the rail and/or between the slide member and the strap to oppose movement of the slide along the rail. In an embodiment, the friction forces are sufficient to resist forces acting on the slide due to gas flow into the interface during use, for example 'blow-off forces', thereby preventing movement of the slide along the rail.

In an embodiment, the, or each, channel is substantially straight. Alternatively one or more channels may be non-linear, that is, they may be curved or may otherwise bend by having wall portions at angles to each other to increase friction between the slide member and the rail and thereby to increase resistance to movement of the slider compared to a straight channel. Each channel may form a tortuous path and/or have one or more pinch points in which the rail is received.

In one embodiment, the strap assembly comprises a pair of rails, and the slide member comprises two oppositely curved or oppositely shaped channels. The channels are shaped such that the transverse spacing between the channels varies along the slider to alter the spacing between the rails as the slider moves along the rails. The spacing between the channels is greatest at or near the ends of the channels, and smallest at or proximal a longitudinal mid-point of the channels.

The slide member may comprise a lock mechanism that is adjustable between an unlocked configuration for allowing movement of the slide member along the rail(s), and a locked configuration for resisting or preventing movement of the slide member along the rail(s). The lock mechanism may be fully or partly housed by the slide member.

In an embodiment, the lock mechanism comprises a cam that is rotatable between an unlocking position and a locking position. When the lock mechanism is in its unlocked configuration the cam is in its unlocking position, and in the locked configuration of the lock mechanism, the cam is in its locking position. In its locking position, the cam presses the rail(s) into a wall of the respective channel. In an embodiment, the cam has a major dimension and a minor dimension, the minor dimension being smaller than the major dimension, for example about 40 to 60% of the major dimension. For example, in one embodiment the strap assembly comprises two rails and two respective channels, with an elliptical cam.

Preferably in the unlocking position a major axis of the cam is substantially parallel with the centreline of the slide member, and in the locking position the major axis of the cam is substantially perpendicular to the centreline of the slide member. That is, the cam may rotate through about 90 degrees from its locking position to the unlocking position. In its locking position the cam presses each rail into a wall of the respective channel to increase frictional forces between the slide member and the rail and thereby increase resistance to movement of the slide member along the strap.

In an embodiment, the lock mechanism may comprise a toggle to toggle the lock mechanism between the locked configuration and the unlocked configuration. In an embodiment, the locking mechanism is mechanically biased into its locking configuration, for example, using a spring.

In an alternative embodiment, the lock mechanism comprises a sliding block housed in the slide member. The block slides longitudinally between an unlocking position and a locking position, wherein in the locking position, the block protrudes into the channel(s) to press the rail(s) into a wall of the respective channel. When the lock mechanism is in its unlocked configuration the block is in its unlocking position, and in the locked configuration of the lock mechanism, the block is in its locking position.

In an embodiment, the block has a transverse dimension at a first part of the block that is greater than a transverse dimension at a second part of the block.

In an embodiment, the block has a transverse dimension at or proximal a first end of the block that is greater than a transverse dimension at or proximal a second part of the block. The slide member and block are preferably oriented such that forces applied to the block and slide member due to tension in the strap urge the locking mechanism towards its locking configuration, thereby automatically 'locking' the strap adjustment during wearing of the headgear. A wearer may move the block out of its locking position, for example using a protruding handle, to adjust the strap.

In a further embodiment, the block has a transverse dimension at or near a middle part of the block that is greater than a transverse dimension at or near an end of the block. Preferably the transverse dimension at or near a middle part of the block is greater than a transverse dimension at or near both ends of the block. The block may comprise curved or straight tapered sides, and the channels may comprise corresponding facing curved or tapered side walls. The sides of the block each define a wall of the channel. In an embodiment, tension in the strap urges the locking mechanism towards its locking configuration, thereby automatically 'locking' the strap adjustment during wearing of the headgear. A wearer may move the block out of its locking position, for example using a protruding handle, to adjust the strap.

In yet a further embodiment, the lock mechanism comprises a rocking member that is pivotable relative to the slide member about a transverse axis. The rocking member can pivot between an unlocking position and a locking position. In an embodiment, the rocking member comprises a base potion that, in the unlocking position does not occlude the channels, and wherein upon adjustment to the locking position, the block protrudes into the channel to press the respective rail into a wall of the channel. When the lock mechanism is in its unlocked configuration the rocking member is in its unlocking position, and in the locked configuration of the lock mechanism, the rocking member is in its locking position.

In an embodiment, the strap comprises a woven textile, for example a single layered non-stretch fabric. The properties of the strap may be non-uniform, for example the strap may vary along the length and/or the width of the strap (in the warp and/or weft directions). In one embodiment, the strap comprises woven threads of varying thread/cord/fibre bundle densities, to vary the width or thickness of the strap. The rail may be provided in this manner by a variation in thickness of the strap.

In an embodiment having rails along the side edges of the strap, the strap is thinned adjacent the side edges to promote curling of fabric material to create or maintain a C-shaped strap cross-section.

In an embodiment, the strap comprises woven threads of different materials to create regions on the strap having different properties. For example, stronger threads may be provided adjacent the, or each, rail to reduce wear and withstand repeated interactions between material and sliding member. Softer or wicking threads may be provided on a skin-contacting region of the strap for comfort.

In an embodiment, the headgear comprises a rear head receiving part to receive a portion of a wearer's head and two strap assemblies. The rear head receiving part of the headgear may be a flexible looped member configured to rest on the crown of a wearer's head. The rear head receiving part may comprise an elastic strap.

The strap assemblies are preferably provided laterally on the headgear. In an embodiment, a first end of each strap is anchored to the head receiving part and a free end of each strap is attached to the respective slide member, for example by being stitched or over moulded in place. Alternatively the first end of each strap may be adjustably attached to the head receiving part.

In an embodiment, the looped portion of the strap may be attached to a respiratory interface, for example through an aperture or around post provided in the frame of the interface, or via a connector attached to the strap that is removably engagable with the frame of the interface.

Also described herein is a patient interface comprising a seal, a frame coupled to the seal, and the headgear described above in relation to the first aspect. The headgear is coupled to the frame.

In an embodiment, the seal is a nasal seal. Alternatively the patient interface may comprise a full-face respiratory interface or an oral seal. In an embodiment, the seal has prongs.

In an embodiment, the frame comprises an inlet for coupling to a fluid supply conduit for the receipt of respiratory gases. The inlet may be threaded to enable removable coupling to the supply conduit. In an embodiment the frame defines a fluid chamber in fluid communication with the inlet and the seal.

In an embodiment, the headgear comprises two strap assemblies, for example side strap assemblies, and the frame comprises two connectors for attaching to the strap assemblies. The connectors may comprise apertures or slots in the frame or a post for the strap to be wrapped around, or be provided by a D-shaped component, or may comprise a hook clip having a post. Each connector preferably slidably receives the strap of the respective strap assembly, for example, the look portion, such that the strap assemblies are adjustable by sliding the strap through or around the connector. The connectors may attach to the strap assemblies via a connector attached to the strap that is removably engagable with the frame of the interface.

This invention may also be said broadly to consist in the parts, elements and features referred to or indicated in the specification of the application, individually or collectively, and any or all combinations of any two or more said parts, elements or features. Where specific integers are mentioned herein which have known equivalents in the art to which this invention relates, such known equivalents are deemed to be incorporated herein as if individually described.

The term 'comprising' as used in this specification and claims means 'consisting at least in part of'. When interpreting statements in this specification and claims that include the term 'comprising', other features besides those prefaced by this term can also be present. Related terms such as 'comprise' and 'comprised' are to be interpreted in a similar manner.

It is intended that reference to a range of numbers disclosed herein (for example, 1 to 10) also incorporates reference to all rational numbers within that range and any range of rational numbers within that range (for example, 1 to 6, 1.5 to 5.5 and 3.1 to 10). Therefore, all sub-ranges of all ranges expressly disclosed herein are hereby expressly disclosed.

As used herein the term '(s)' following a noun means the plural and/or singular form of that noun. As used herein the term 'and/or' means 'and' or 'or', or where the context allows, both.

BRIEF DESCRIPTION OF THE DRAWINGS

Embodiments will now be described by way of example only and with reference to the accompanying drawings in which:

FIG. 5(*iv*) is a section view of the assembled strap and slide member, taken through the slider;

Figure 6:
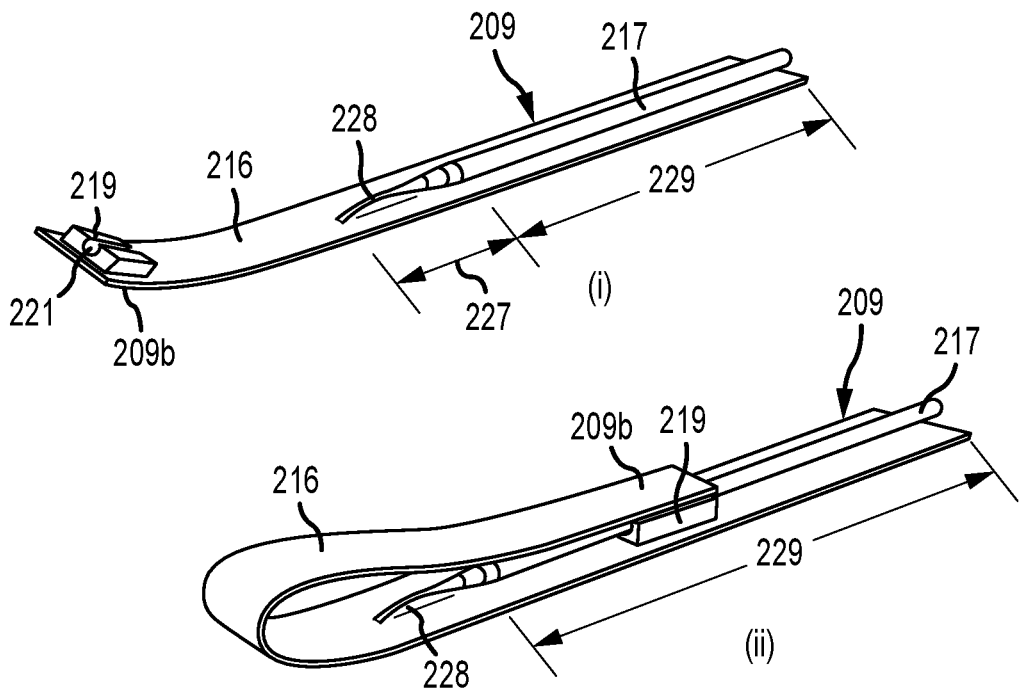
FIGS. 6(*i*) and (*ii*) are perspective views illustrating an exemplary tapered rail lead-in portion, where FIG. 6(*i*)
Figure 7:
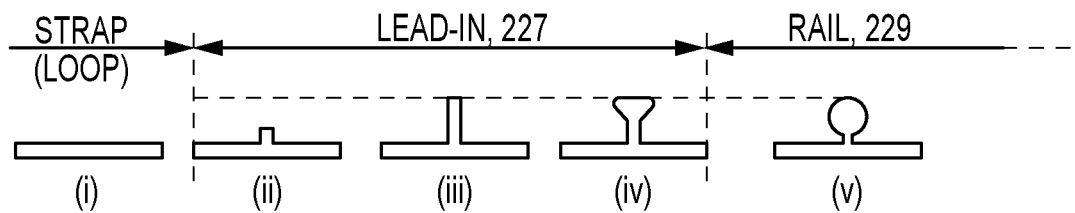
Figure 8:
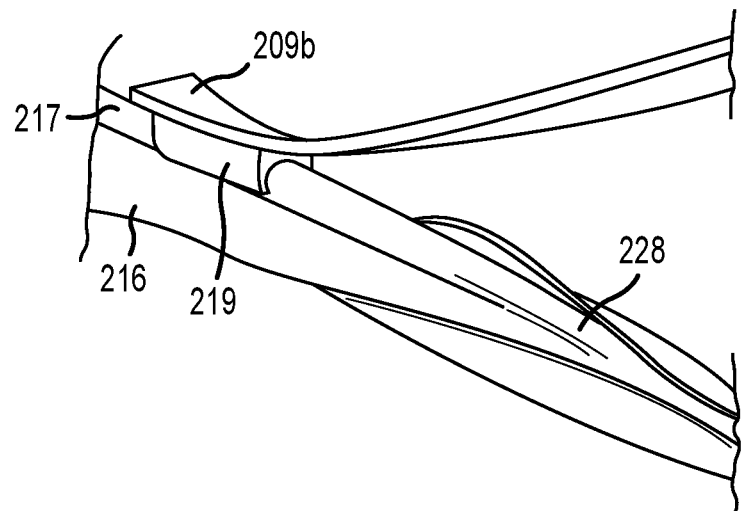
Figure 9:
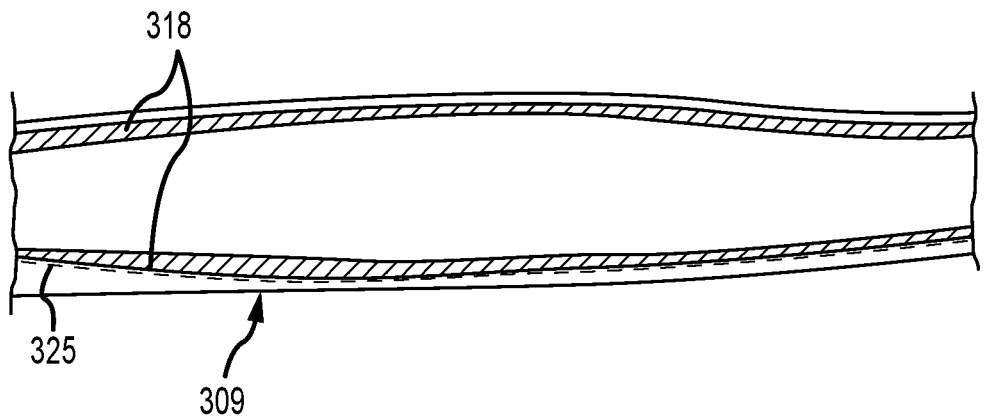
Figure 10:
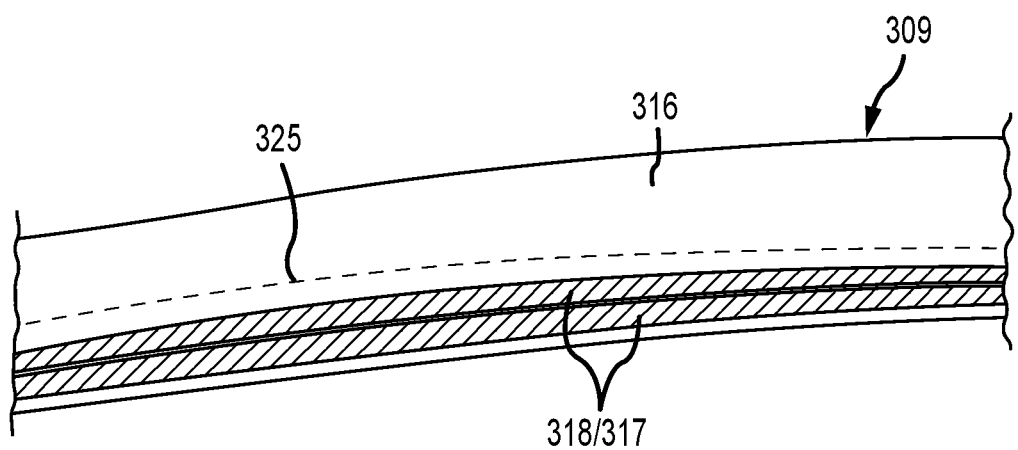
Figure 11:
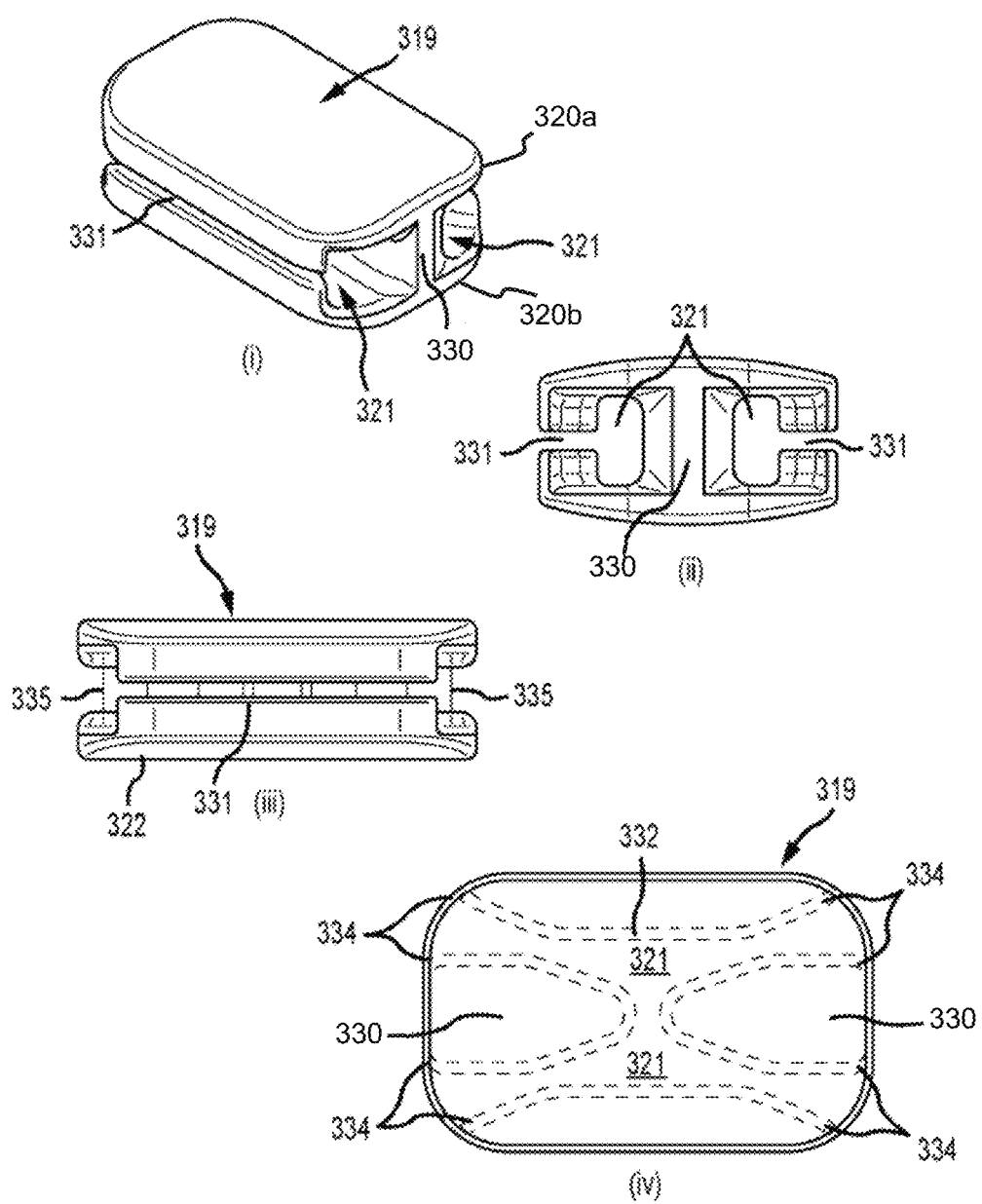
Figure 12:
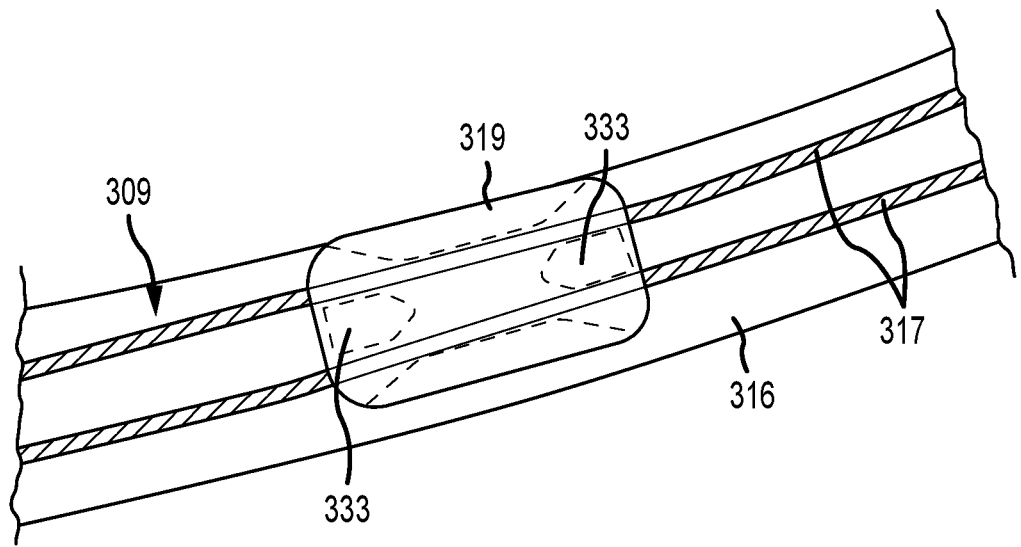
Figure 13:
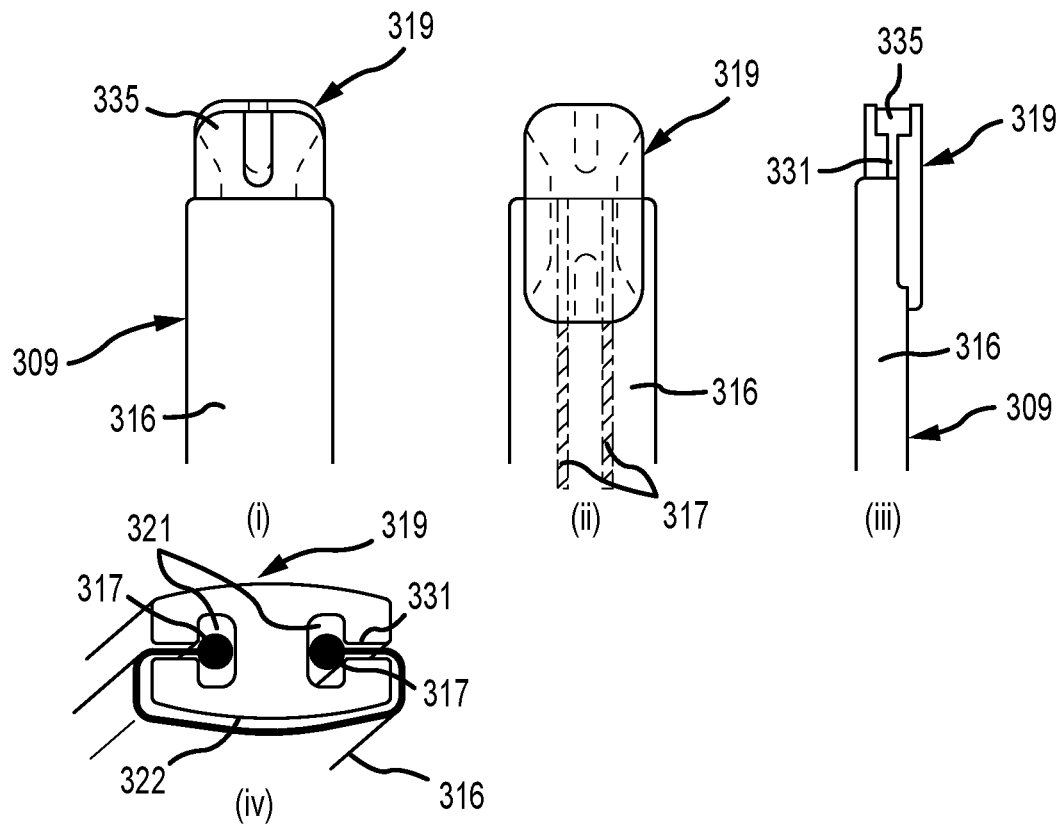
Figure 14:
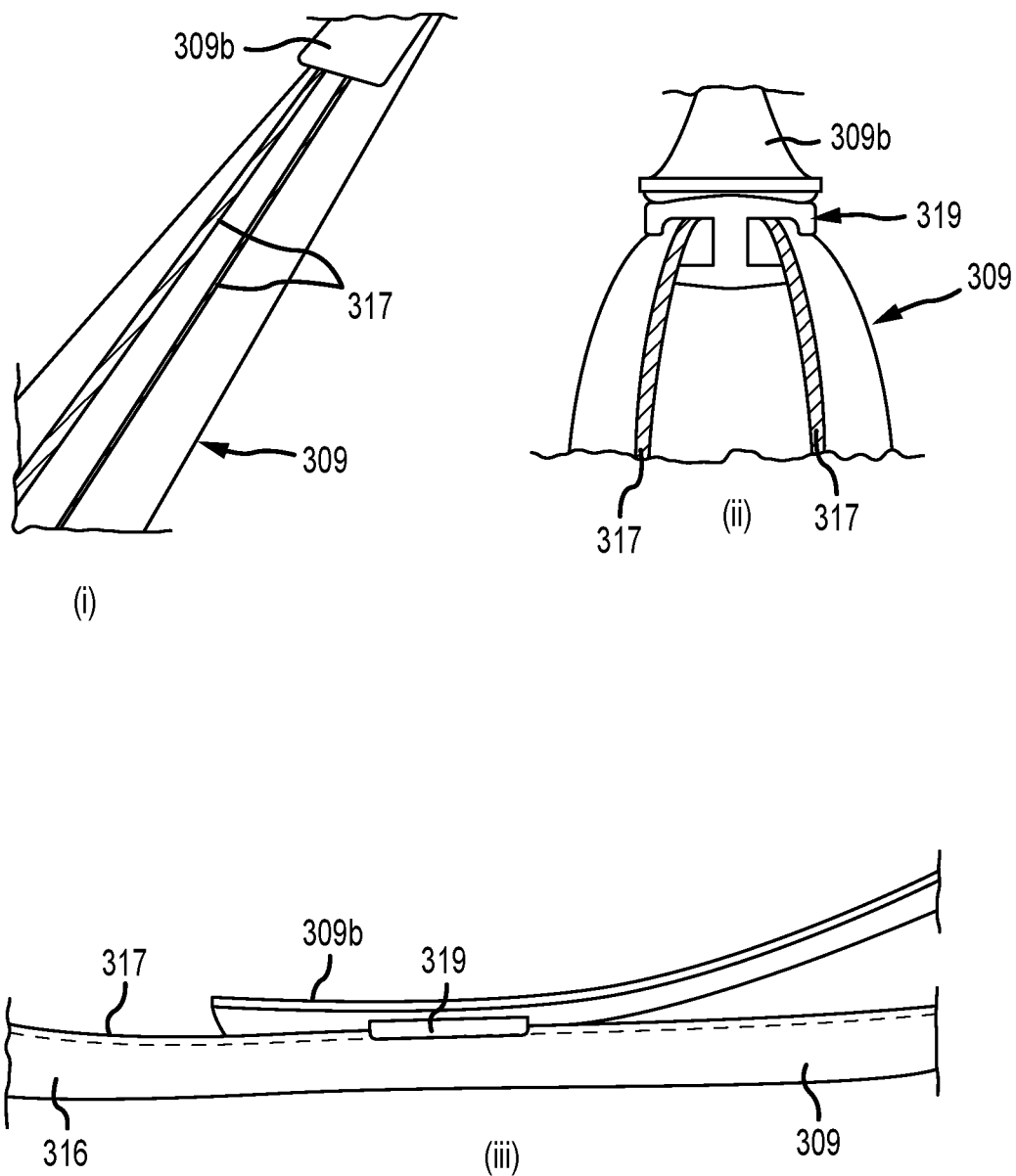
Figures 15, 16:
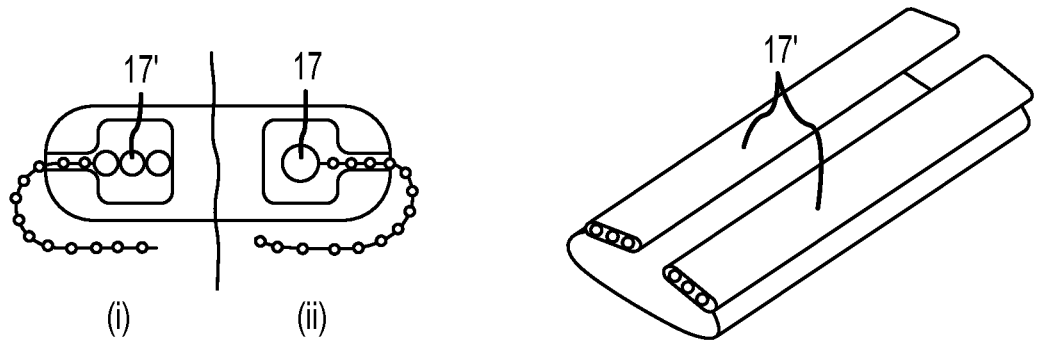
Figure 17:
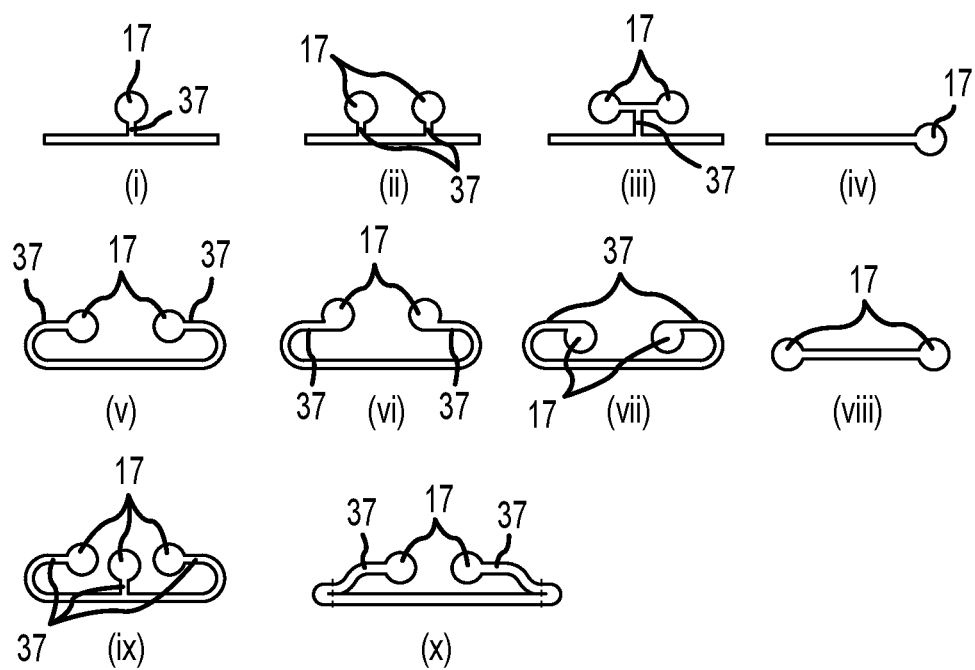
Figure 18:
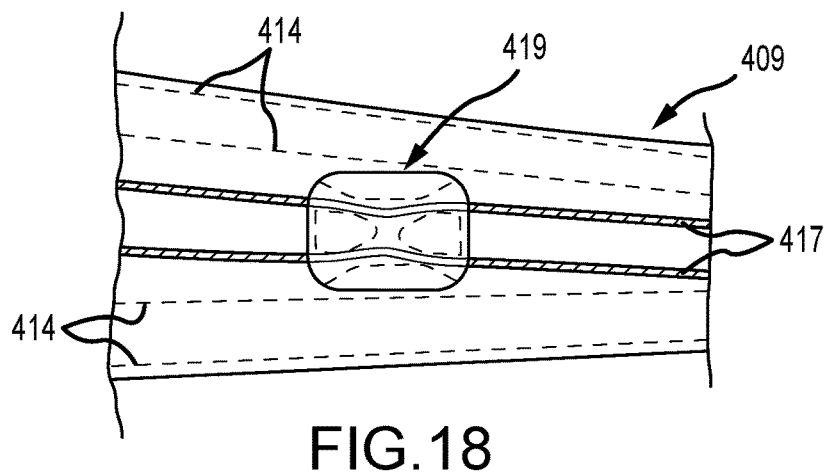
Figure 19:
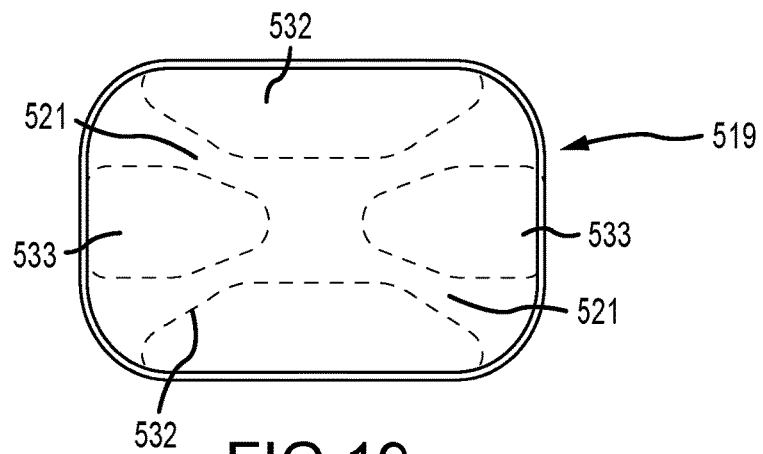
Figure 20:
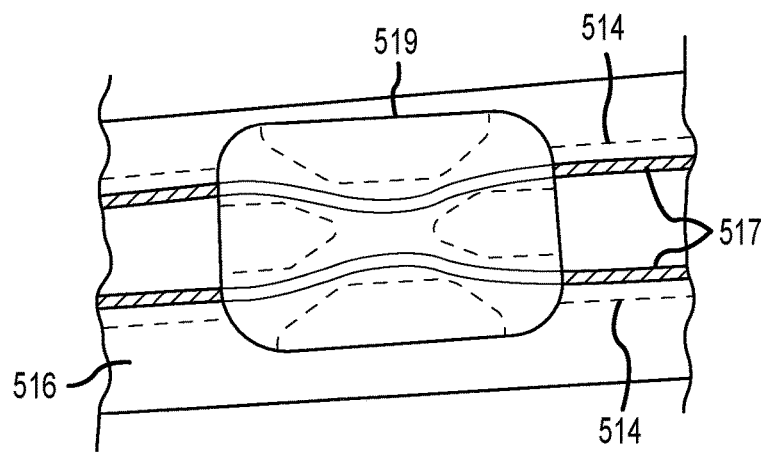
Figure 25:
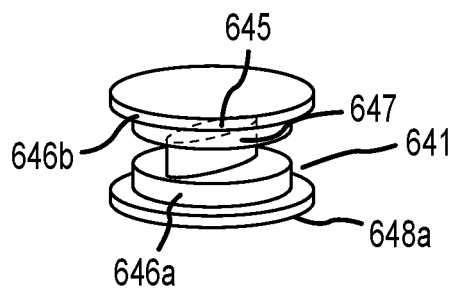
Figure 26:
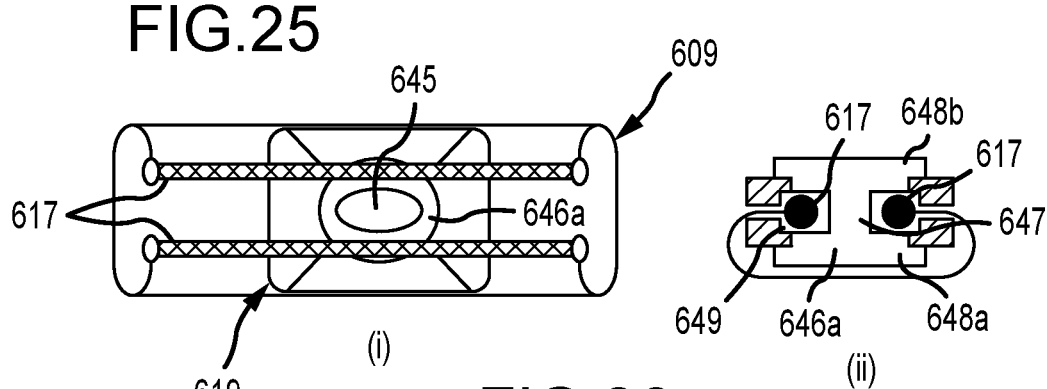
Figure 27:
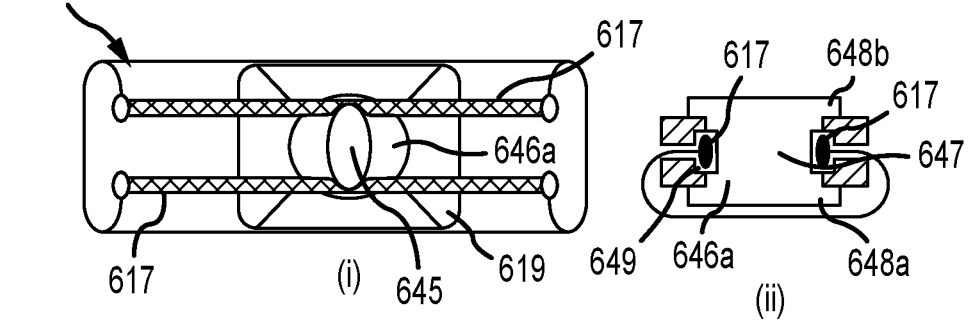
Figure 28:
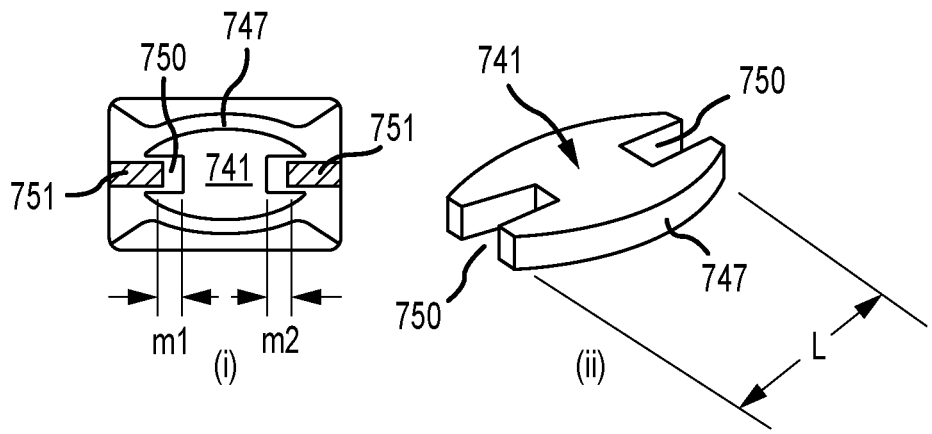
Figure 29:
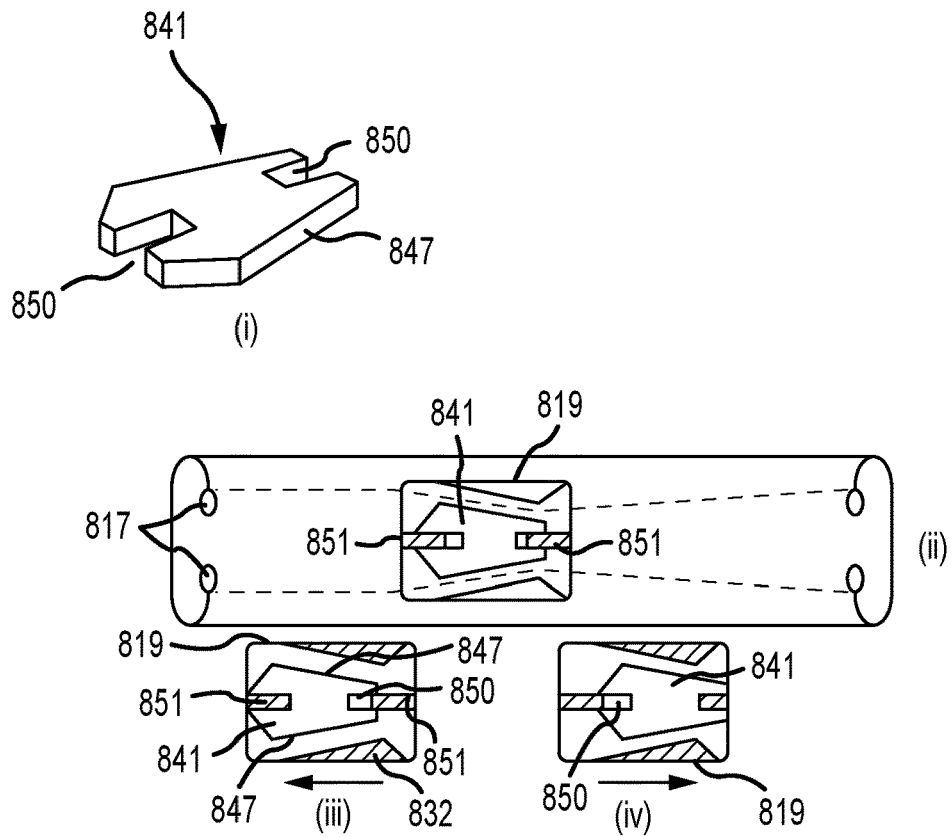
Figure 30:
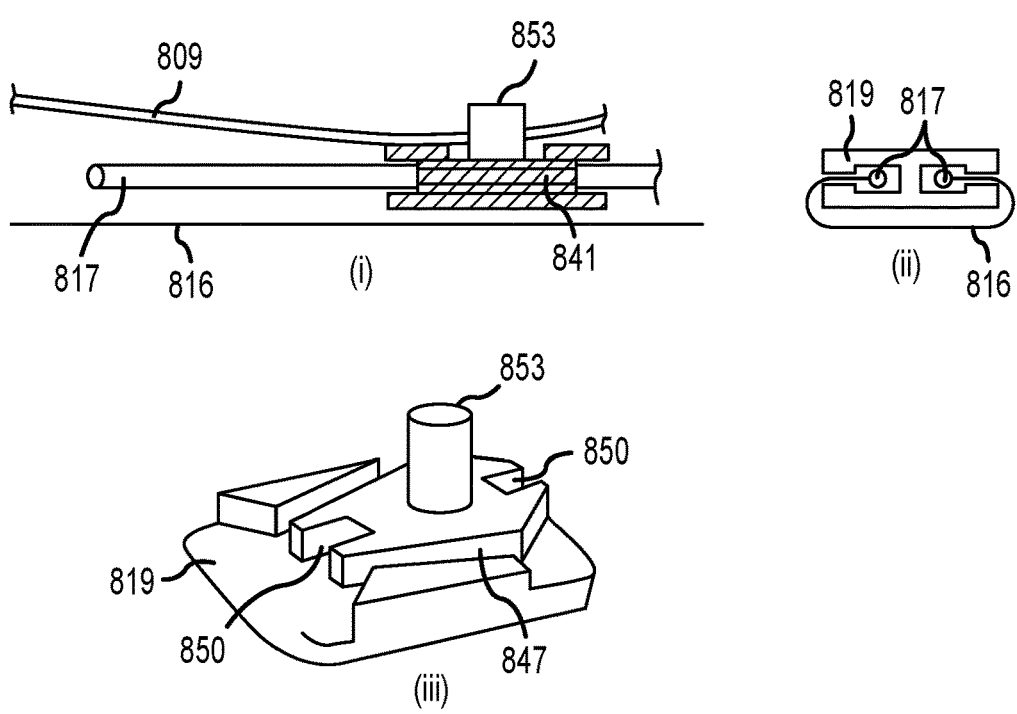
Figure 31:
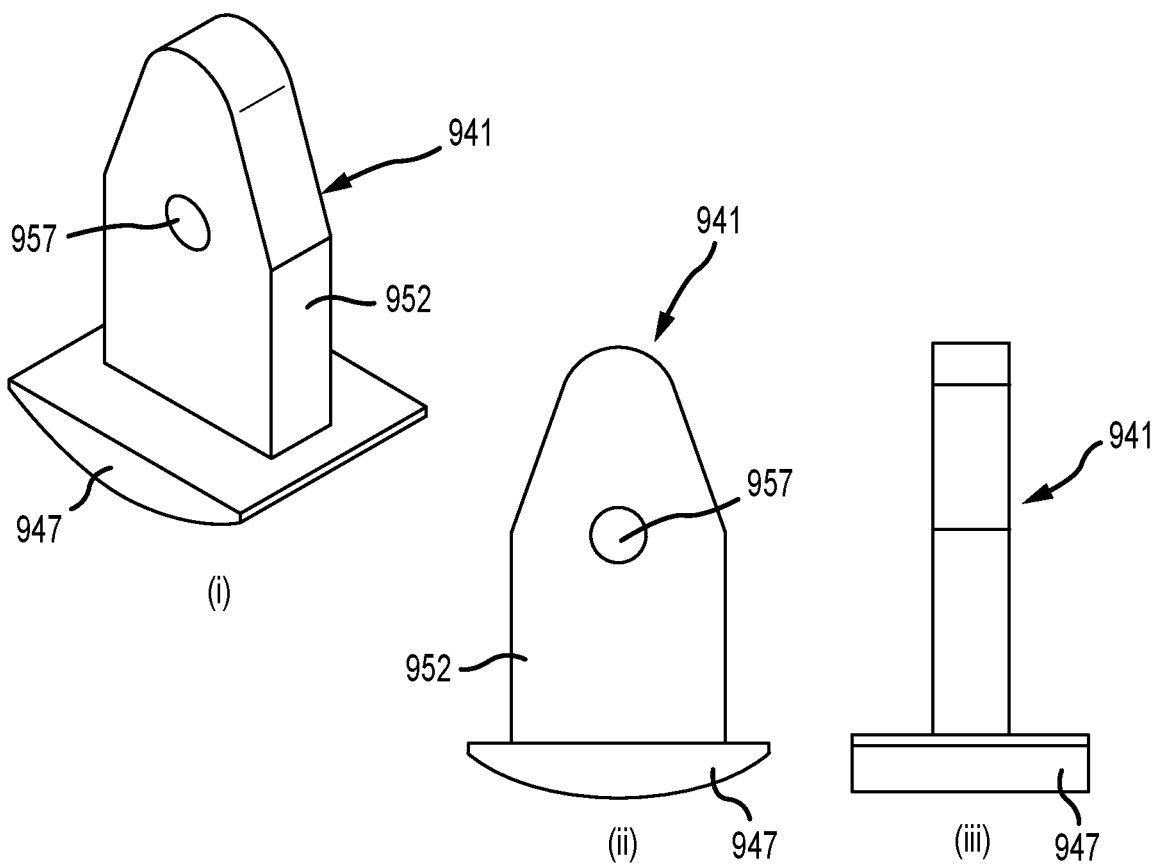
Figure 32:
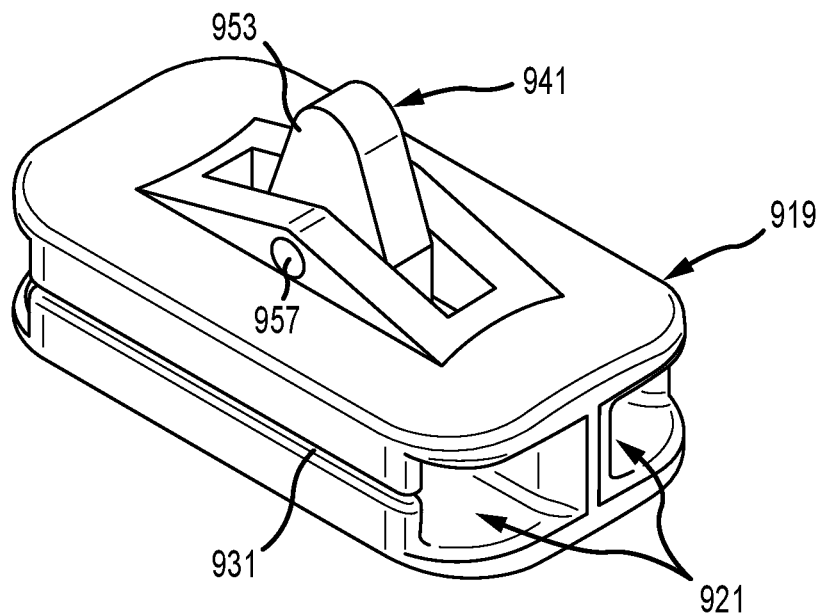
Figure 33:
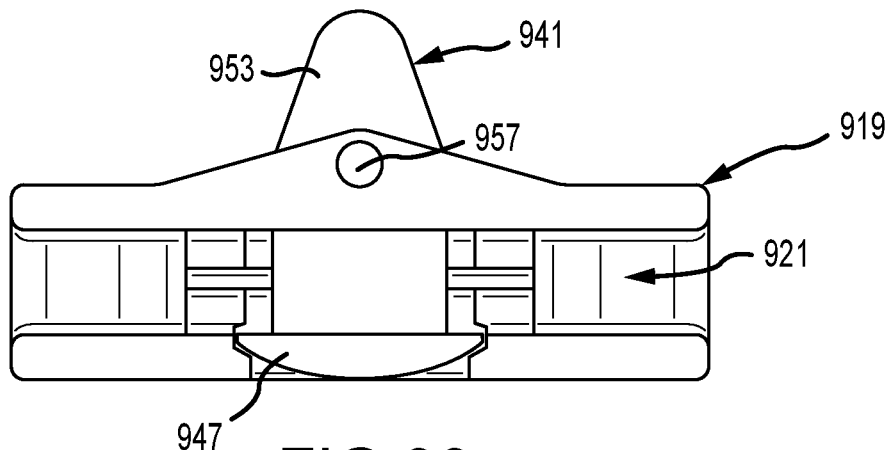
Figure 34:
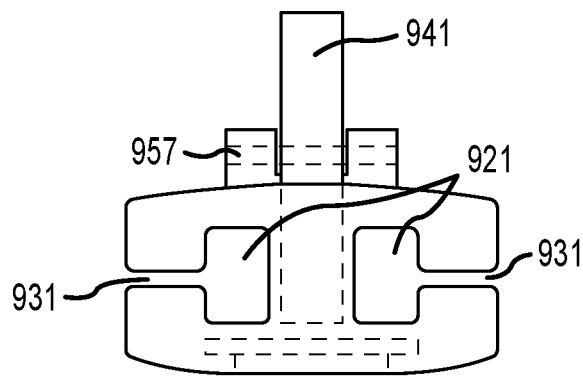
Figure 35:
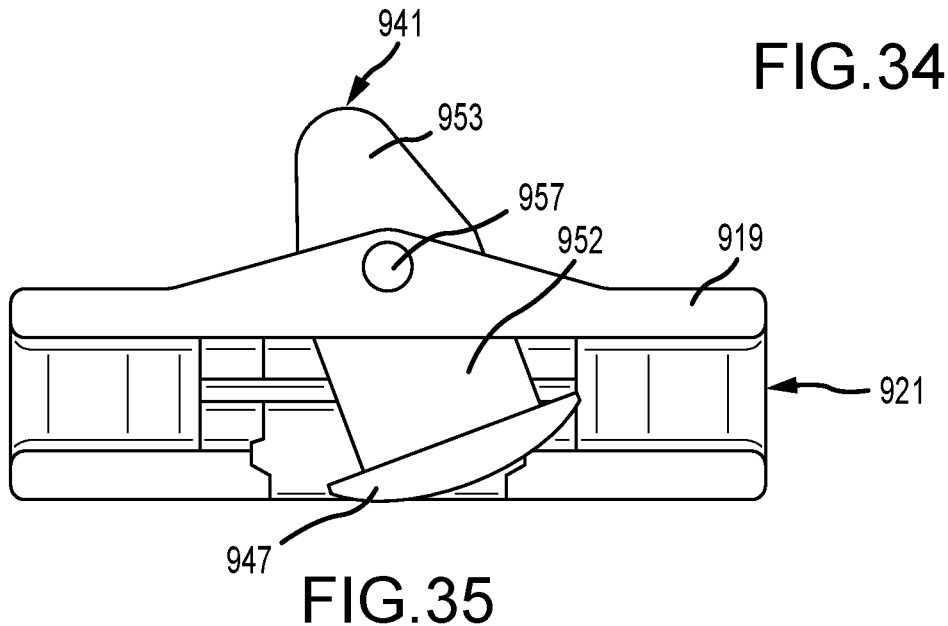
Figure 36:
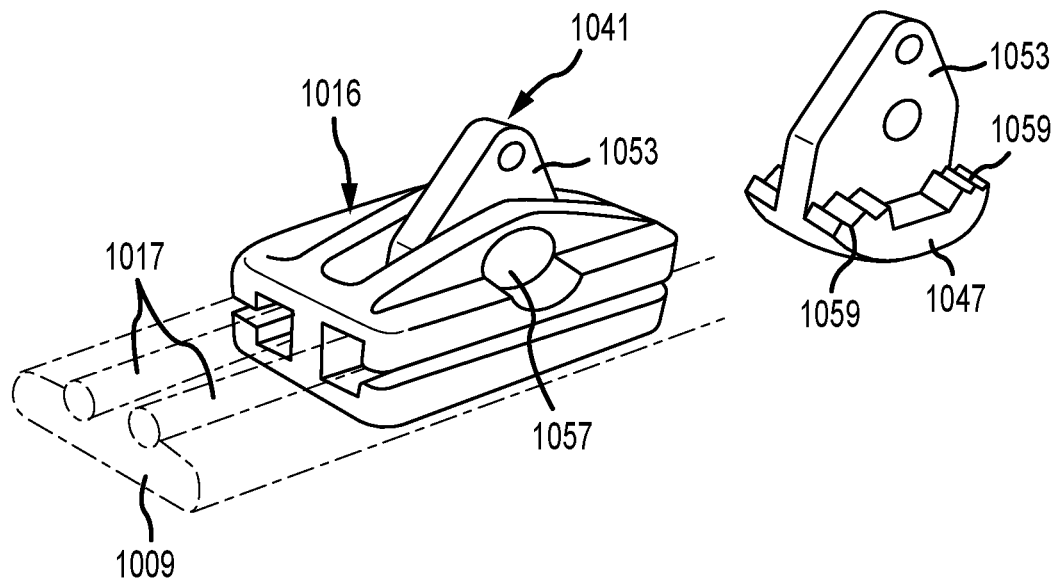
Figure 37:
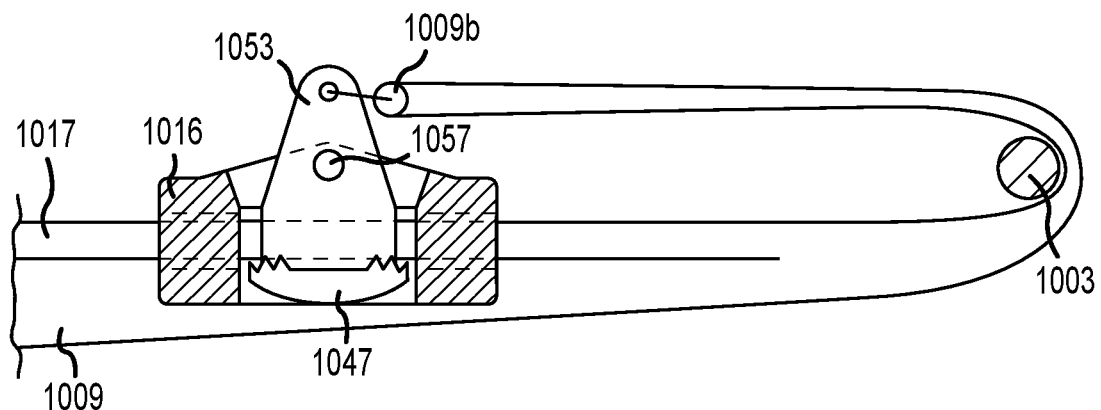
Figure 41:
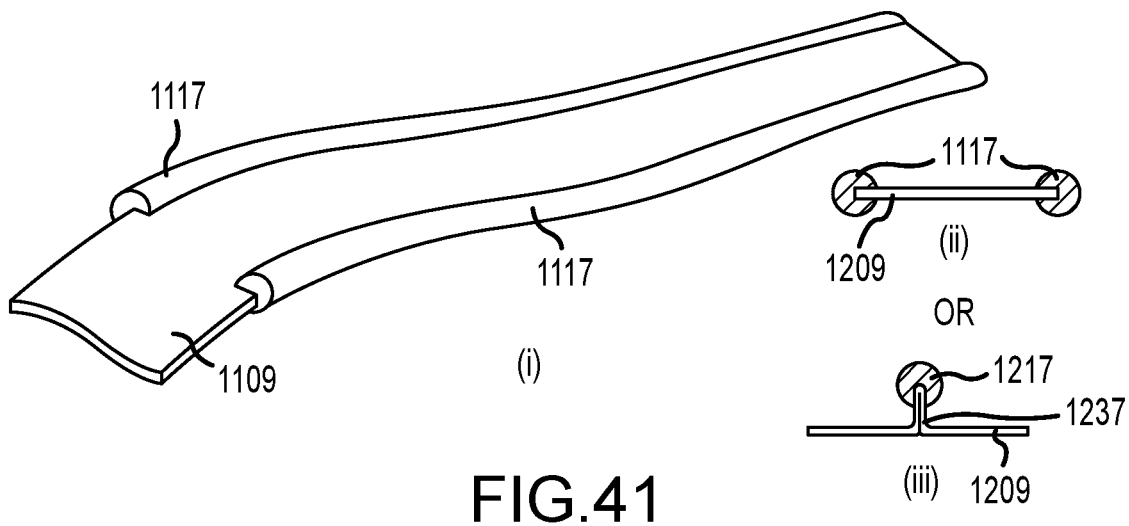
Figure 42:
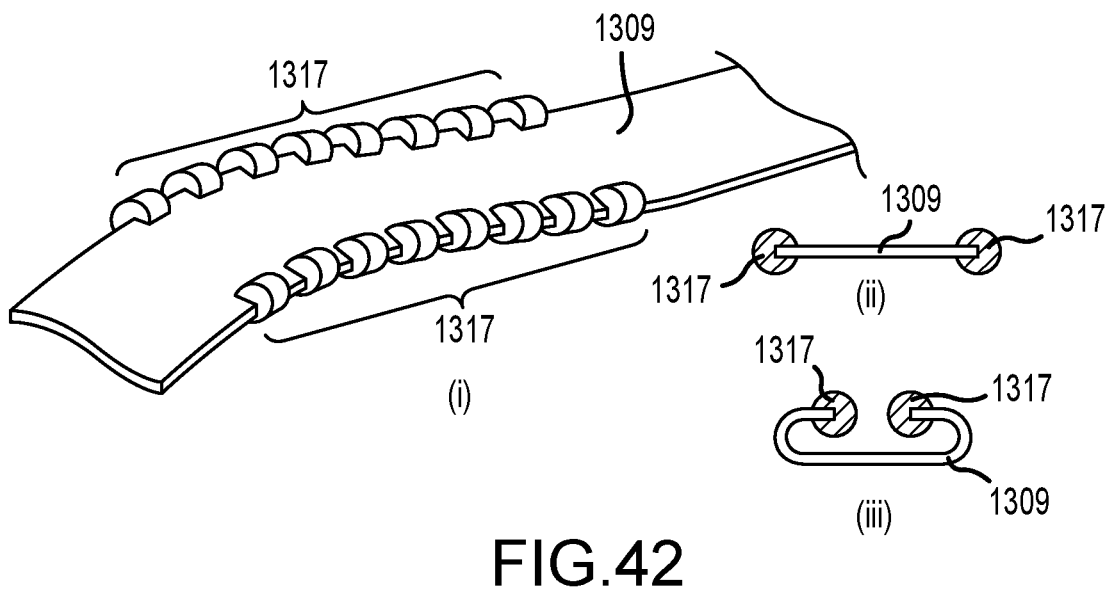

shows the slide member attached to the free end of the strap but not yet engaged with the rail, and FIG. 6(ii) shows the slide member engaged with the rail;

FIGS. 7(i) to (v) are cross section views through the strap of FIG. 6(i) illustrating the profile of the lead-in portion, where FIG. 7(i) is a section of the strap taken on the free end side of the lead-in, FIG. 7(ii) is taken near the beginning of the lead-in portion, FIG. 7(iii) is taken near a mid-point of lead in portion, FIG. 7(iv) is taken near the transition between the lead-in and the rail, and FIG. 7(v) is a section taken through the rail;

FIG. 8 is a perspective view of an adjustable strap with a gradually tapering lead-in at the start of the rail and folded strap edges;

FIG. 9 is a top view of a further embodiment headgear strap having two side rails; FIG. 10 is a side perspective view of the strap of FIG. 9;

FIGS. 11(i) to (iv) show a first embodiment slide member for use on a strap having two rails, where FIG. 11(i) is a perspective view of the slide member, FIG. 11(ii) is an end elevation view, FIG. 11(iii) is a side elevation view, and FIG. 11(iv) is a top view;

FIG. 12 is a top view showing the slide member of FIGS. 11(i) to (iv) installed on the strap of FIGS. 9 and 10;

FIGS. 13(i) to 13(iv) illustrate the engagement of the slide member of FIGS. 11(i) to (iv) with the strap of FIGS. 9 and 10, where FIG. 13(i) is a bottom view of the slide member partially engaged with the strap, FIG. 13(ii) is a top view, FIG. 13(iii) is a side view, and FIG. 13(iv) is an end view;

FIGS. 14(i) to 14(iii) further illustrate the engagement of the slide member of FIGS. 11(i) to (iv) with the strap of FIGS. 9 and 10, with the free end of the strap shown attached to the slide member, where FIG. 14(i) is a perspective view, FIG. 14(ii) is an end perspective view, and FIG. 14(iii) is a side view;

FIGS. 15(i) and (ii) are end views illustrating the engagement of a slide member with strap rails, where FIG. 15(i) illustrates a rail formed from a plurality of adjacent cords, and FIG. 15(ii) shows a rail formed from a single cord;

FIG. 16 is a perspective view of a rail portion of a strap for the arrangement of FIG. 15(i), having two rails each comprising three cords;

FIGS. 17(i) to (x) are schematic cross section views of a rail portion of a strap showing a number of exemplary alternative embodiments having different rail arrangements;

FIG. 18 is a top perspective view of a slide member positioned on a strap having the profile shown in FIG. 17(x);

FIG. 19 is a top view of a second embodiment slide member;

FIG. 20 is a top view of the slide member of FIG. 19 engaged with a rail such as the one in FIG. 17(v), with the rail being deformed at a mid-region of the slide member;

FIG. 21 is a further top view corresponding to FIG. 20 showing a section view of the slide member;

FIGS. 22(i) and (ii) are section views of the strap and slide member arrangement of FIGS. 20 and 21, where FIG. 22(i) is taken through line AA of FIG. 21, and FIG. 22(ii) is taken through line BB of FIG. 21;

FIG. 23 is a top view of a further embodiment slide member engaged with a strap having two rails, the slide member has a rotatable locking component that is hidden in this view for clarity;

FIGS. 24(i) and 24(ii) show the slide member of FIG. 23, with the rotatable locking component removed, where FIG. 24(i) is a perspective view and FIG. 24(ii) is a section view taken through a mid-point of the slide;

FIG. 25 is a perspective view of the rotatable locking component for use in the slide member of FIGS. 23 to 24(ii);

FIGS. 26(i) and (ii) show the embodiment of FIG. 23, where FIG. 26(i) is the view of FIG. 23 but showing the rotatable locking component in an unlocking position, and FIG. 26(ii) is a section view taken through a mid-point of the slider in FIG. 27(i), showing the strap rails uncompressed;

FIGS. 27(i) and (ii) are views relating to the embodiment of FIGS. 23 and 26(1) and 26(ii), where FIG. 27(i) shows the view of FIG. 26(i) but with the rotatable locking member rotated to its locking position, and FIG. 27(ii) is a section view taken through a mid-point of the slider in FIG. 27(i), showing the strap rails compressed;

FIGS. 28(i) and (ii) show one embodiment slider with a longitudinally movable locking member, where FIG. 28(i) is a top view of a section through the slide member showing the locking member slidably held in the slider housing, and FIG. 28(ii) is a perspective view of the locking member of FIG. 28(i);

FIGS. 29(i) to (iv) show a further embodiment slider with a longitudinally movable locking member, where FIG. 29(i) is a perspective view of the core member, FIG. 29(i) is an illustrative top view of a section through the slide member showing the locking member slidably held in the slide member housing and receiving the strap rails, FIG. 29(iii) is an illustrative view showing the locking mechanism in an unlocked open position, and FIG. 29(iv) is an illustrative view showing the locking mechanism in a locking configuration;

FIGS. 30(i) to (iii) are further views showing the slide member of FIGS. 29(i) to 29(iv), where FIG. 30(i) is a side section of the side member and strap, FIG. 28(i) is an end view, and FIG. 30(iii) is a perspective view of the side member with the top portion of the housing removed for clarity;

FIGS. 31(i) to (iii) show a rocking locking component for pivotally mounting to the slide member, where FIG. 31(i) is a perspective view, FIG. 31(ii) is a side elevation view, and FIG. 31(iii) is an end elevation view;

FIG. 32 is a perspective view of a slide member having the rocking locking member of FIGS. 31(i) to (iii);

FIG. 33 is a side section view of the slide member of FIG. 31, with the section taken through a side channel, showing the locking component in an unlocking position;

FIG. 34 is an end view of the slide member of FIGS. 31(i) to 33;

FIG. 35 is a view corresponding to FIG. 33 but with the locking component shown in a locking position;

FIGS. 36(i) and (ii) show a further embodiment slider having a rocking locking member with strap engaging teeth, where FIG. 36(i) is a perspective view of the slider, and FIG. 36(ii) is a perspective view of the rocking locking component;

FIG. 37 is a side section of the sider of FIG. 36(i) on a strap;

FIGS. 38(i) and 38(ii) are illustrations showing the warp and weft of one embodiment uniform strap using a single type of yarn, where FIG. 38(i) is a schematic perspective view, and FIG. 38(ii) is a section view of FIG. 38(i) taken along the weft direction;

FIGS. 39(i) and 39(ii) illustrate the warp and weft of a further embodiment strap using multiple yarns of varying thicknesses or properties, where FIG. 39(i) is a schematic perspective view, and FIG. 39(ii) is a section view of FIG. 39(i) taken along the weft direction;

FIG. 40 illustrates an exemplary method of manufacturing for a strap having a varying width and comprising yarns of different thicknesses;

FIGS. 41(*i*) to 41(*iii*) illustrate an alternative embodiment strap having a continuous overmoulded rail, where FIG. 41(*i*) is a perspective view of a flat strap having two side rails, FIG. 41(*ii*) is a cross sectional view of the embodiment of FIG. 41(*i*), and FIG. 41(*iii*) is a cross sectional view of an embodiment having a single central continuous overmoulded rail; and FIGS. 42(*i*) to 42(*iii*) illustrate a further alternative embodiment strap having a segmented overmoulded rail, where FIG. 42(*i*) is a perspective view of a flat strap having two side rails, FIG. 42(*ii*) is a cross sectional view of the embodiment of FIG. 42(*i*), and FIG. 42(*iii*) is a cross sectional view of the strap of FIGS. 42(*i*) and 42(*ii*) is folded or curved to form a C-shape.

DETAILED DESCRIPTION

Various embodiments and methods of manufacture will now be described with reference to FIGS. 1 to 40. In these figures, like reference numbers are used in different embodiments to indicate like features, with the addition of a multiple of 100. Directional terminology such as the terms 'front', 'rear', 'upper', 'lower', and other related terms are used in the following description for ease of description and reference only, it is not intended to be limiting. The forward direction or top of a component is not necessarily related to the orientation of the component when the headgear is worn by a user.

Figure 1:
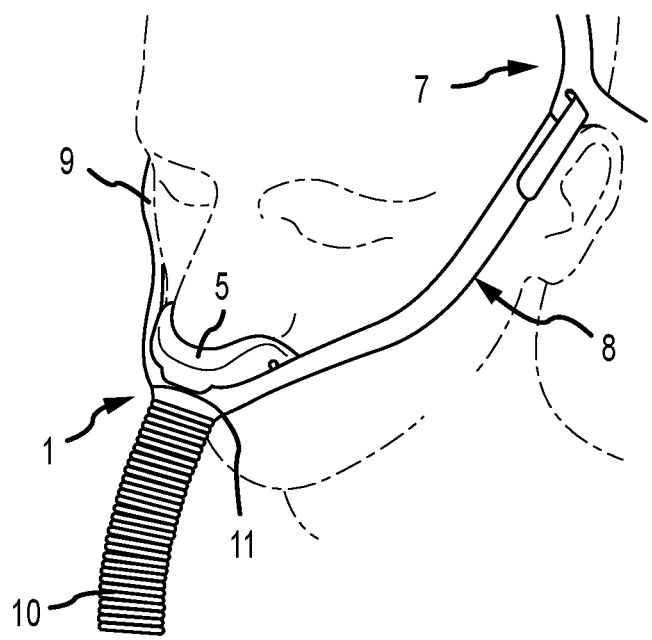
FIG. 1 is an illustrative view showing a user wearing an exemplary respiratory user interface including headgear with adjustable side straps, a frame, and a nasal seal, the interface being connected to a supply conduit.

FIG. 1 shows and exemplary embodiment nasal respiratory interface 1. The respiratory interface comprises a nasal seal 5 and frame with connectors 3, and headgear 7 connected to the connectors 3. A fluid supply conduit 10 is coupled to a fluid inlet 11 on the frame for the supply of breathing gasses to a user. The nasal seal 5 seals with the face of a user and has prongs 6 for positioning at least partly in or at the base of the nares to supply respiratory gasses nasally to the user.

Figure 2:
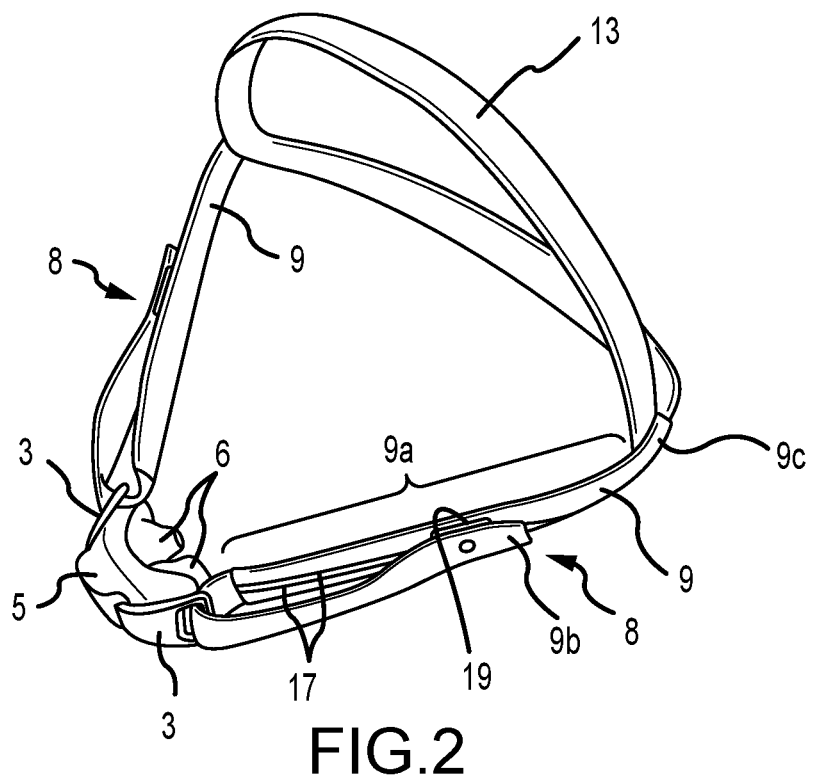
FIG. 2 is a view of an exemplary respiratory interface and removed from the user and with the supply conduit disconnected.
Figure 3:
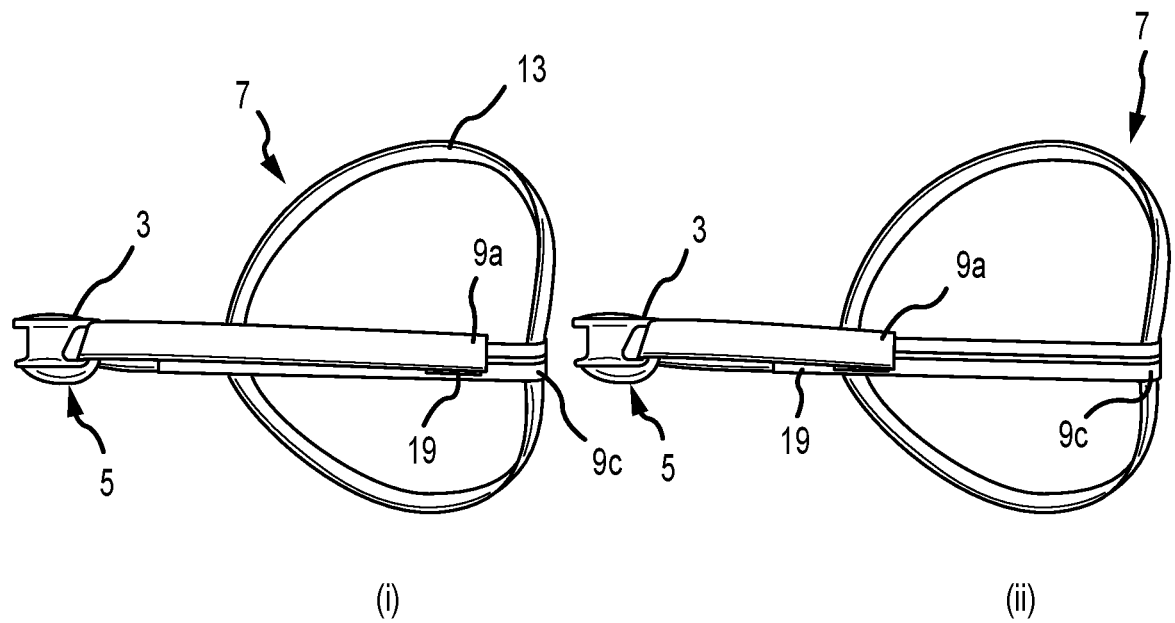
FIGS. 3(*i*) and (*ii*) are side views of the headgear from the respiratory interface of FIG. 2, where FIG. 3(*i*) shows adjustable side strap adjusted to a shortened configuration, and FIG. 3(*ii*) shows the adjustable side strap adjusted to a lengthened configuration.

FIGS. 2 to 3(*ii*) show a first embodiment of the headgear 7. The headgear 7 comprises a rear portion 13 anchoring the headgear on a user's head, and two laterally positioned adjustable strap assemblies 8 extending between the rear portion 13 and the respiratory interface 1. In the embodiment shown, the rear portion 13 is a loop that is sized for placing over or near the crown of a wearer's head. The base of the rear portion 13 may rest on the nape of the wearer's head. Both the rear portion 13 and the lateral straps 9 comprise a flexible material such as a textile or elastomer. The rear portion 13 in particular may comprise an elastic material to allow the rear portion 13 to stretch for a more secure fit. Alternatively, the rear portion may comprise a rigid and/or non-elastic material.

The headgear 7 comprises at least one strap assembly 8 comprising a flexible strap 9 with at least one rail 17 extending longitudinally along a rail portion 9*a* of the strap, and a slide member 19 that is slidable along the rail. The headgear 7 in the embodiment shown has two laterally positioned slide assemblies 8, but alternative embodiment headgear may have more or fewer strap assemblies 8. For example, the headgear 7 may four-strap assemblies 8, and/or may have one or more strap assemblies 8 on the rear and/or crown portions 9 of the headgear.

The strap assembly slide member 19 has a channel for receiving and sliding on the rail 17, and a further portion of the strap at or near a free end of the strap is fixedly attached to the slide member at an attachment point. The length of the strap assembly 8 is adjustable by sliding the slide member 19 along the rail 17.

The rail portion 9*a* of the strap is the portion of the strap that has the rail extending along it. It is to be appreciated that the rail may extend only along a part of the strap and that other parts of the strap may not have the rail thereon.

Each strap 9 has a free end 9*b* and an anchoring end 9*c* that is attached to the rear portion 13 of the headgear or alternatively anchored to the respiratory interface 1. In the embodiment shown, the anchoring end 9*c* of each lateral strap 9 is fixed to the rear portion 13 by being stitched in place 14. Alternatively the anchoring end 9*c* may be movably mounted to the rear portion 13 such that the position or orientation of the lateral straps 9 may be adjusted relative to the rear portion 13.

The rail portion of the strap 9 is folded over on itself to form the rails and the slide member is slidably attached to the rails. The strap is also attached to the slide member 19 at or near a free end 9*b* of the strap 9. That is, the slide member 19 attaches to the strap both at, or near, the free end of the strap 9*b*, and slidably to the rail portion of the strap 9*a* via the rail or rails 17. This creates a loop 15 in the strap to facilitate connection to a strap anchor point on the user interface or headgear 7, for example by looping over a post. Sliding the slide member 19 along the rail or rails 17 moves the free end 9*b* of the strap towards or away from the attached end 9*c*, changing the size of the loop 15 and thereby the length of the strap assembly 8. As illustrated in FIG. 3(*ii*), sliding the slide member 19 towards the anchoring end 9*c* lengthens the loop 15 and shortens the strap assembly 8; whereas sliding the slide member 19 away from the anchoring end 9*c* shortens the loop 15 to lengthen the strap assembly 8.

Figure 4:
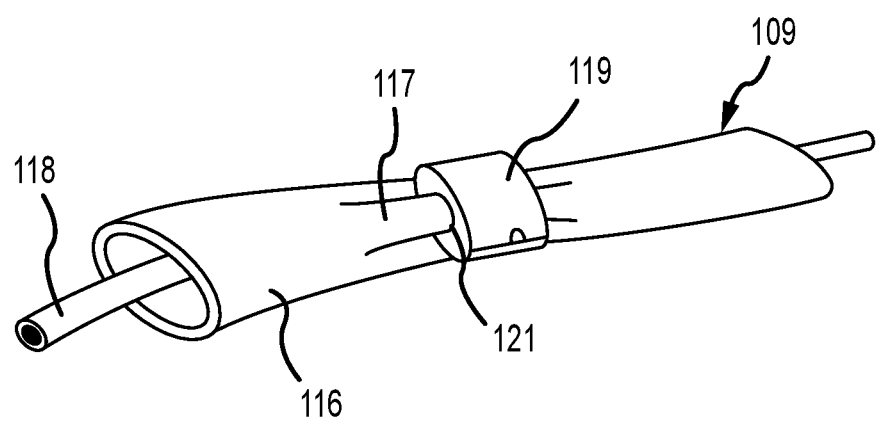
FIG. 4 is an illustrative perspective view of a first embodiment strap and slide member, only a portion of the strap is shown and the free end of the strap ordinarily attached to the slider is hidden for clarity.

The rail 17 acts as an elongate track for the slide member 19 to slide along. In some embodiments, the rail is provided by a cord that extends at least along the rail portion of the strap 9. FIG. 4 illustrates one such embodiment.

In the embodiment of FIG. 4, the strap 9 is tubular, with a cord 118 running longitudinally along the hollow of the tube. The top surface of the strap 9 provides a surface for the slide member to bear against as it slides along the rail portion, and the opposite under surface of the tube rests against the wearer's skin. The strap 109 and cord 118 are not continuously attached along the length of the cord, such that a rail may not be visible along the length of the rail portion and the cord 118 may be free to move relative to the tubular strap 109 within the hollow of the strap.

The slide member 119 is a rigid component comprising a substantially linear channel 121 opening to the underside of the slide member. The body of the slide member 119 preferably comprises a shape with rounded and/or tapered edges so that the slide member is able to rest against a user with minimal discomfort that may be caused by sharp, square edges.

The channel 121 is a keyhole-type channel, with its opening 131 forming an open ended slot on the underside of the slide member 119. The cross-sectional profile of the channel consists of a main portion that receives and retains the cord 118 (along with the strap fabric which becomes wrapped tightly around the perimeter of the cord 118), and a necked portion that necks in at or near the channel opening 131 at the base of the slide member 117. For example, the channel may have an omega ($\Omega$) shaped cross-sectional profile.

Figure 5:
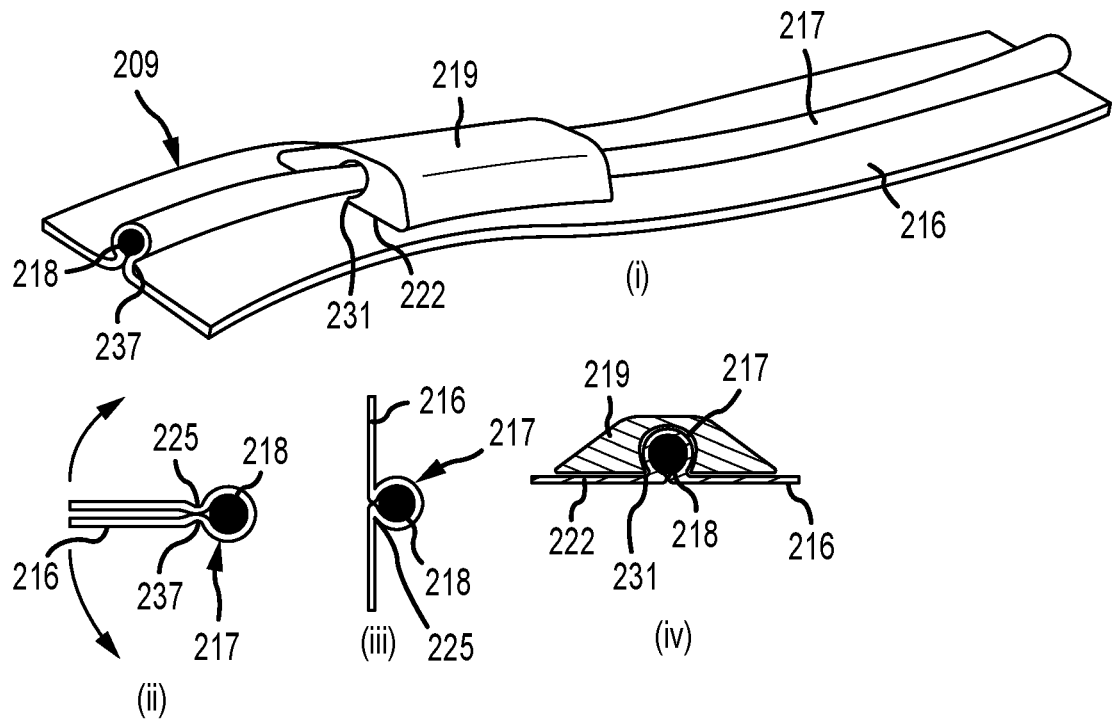
FIGS. 5(*i*) to (*iv*) are views of a second embodiment strap and slide member, only a portion of the strap is shown and the free end of the strap ordinarily attached to the slider is hidden for clarity, where FIG. 5(*i*) is a perspective view, FIG. 5(*ii*) is an end view of the strap illustrating the method of creating the rail, FIG. 5(*iii*) is an end view of the strap.

The main portion of the channel has a cross-section to accommodate the rail depending on the shape and properties of the rail. The rail preferably volumetrically occupies at least a major part of the main portion of the channel, for example by the shape of the cross section closely matching the cross-section of a rigid rail, or the cross-sectional area being substantially the same as the cross-sectional area of a compressible or compliant rail such as a braided bead. As an example, the cross-section of the main portion may be substantially circular, elliptical, rectangular, or a approximating a trapezoid as shown in the embodiment of FIG. 5.

The necked portion at the opening 131 has a width that is less than the diameter of the cord 118 to ensure the cord is retained within the channel 121 as the slide member 119 moves along the rail, by preventing the slide member 119 being moved perpendicularly off the rail. The narrower the neck 131 in relation to the rail, the more effective it is at preventing derailing of the slide member.

In the embodiment of FIG. 4, the slide member channel 121 forces strap fabric to tightly wrap around over the cord 118 along the length of the slide member channel 121. The narrowing at the channel opening 131 pinches the strap 109 together under the cord 118 to form a web bridging between the rail and the flat portion of the strap. As the slide member 119 is moved along the cord 118, the strap is guided and pinched around the cord at the leading end of the slide member until it is released from the cord at the trailing end of the slide member.

In alternative embodiments, the strap 109 may be permanently wrapped around the cord 118 to form a visually distinct permanent rail along the rail portion of the strap. Such an embodiment is less likely to encounter resistance due to relative movement between the cord 118 and the strap 109. FIGS. 5(*i*) to (*iii*) show one such embodiment in which the cord 218 is enveloped by the strap 209. The strap 209 is wrapped around the cord and stitched along a stitch line 225 close to the base of the cord. Alternatively the strap may be welded or otherwise attached using a suitable method. To do this, the strap is typically folded over the cord as illustrated in FIG. 5(*ii*), the fabric layers stitched together adjacent the cord 218, before folding the strap out as shown in FIG. 5(*iii*) to create a defined rail 217 that is received by the channel 221 in the slide member 219. The stitch line 225 forms a web 237 immediately adjacent the stitch line 225, between the rail and the flat surface of the strap.

The narrowed opening 231 of the channel 219 runs generally along the line of the stitching 225 to receive the fabric layers near where they are joined together. In the embodiment shown, the rail 217 runs longitudinally along or near a mid-line of the strap.

Rather than using a cord, alternatively, the folded strap (FIG. 5(*ii*)) may be stitched together along a stitch line spaced from the fold line with the cord omitted. When folded out, the strap then comprises a longitudinal rail formed by the protruding folded/looped fabric, which forms the rail. For such embodiments, the stitching preferably compresses the strap material along the stitch line to provide a narrowed web for receipt by the channel opening so the width of the folded rail is greater than the thickness of the web to reduce the likelihood of the slide member being pulled off the rail.

Referring to FIGS. 41(*i*) to 42(*iii*), as a further embodiment, the rail(s) 1117, 1217, 1317 may be formed by overmoulding a plastic material such as silicone, TPU or TPE along a length of the strap, the overmoulded portion creating a portion with an enlarged width compared to the strap, or a protruding portion. Each overmoulded rail 1317 may comprise a plurality of segments that are spaced apart along an edge of the strap 1309. By providing the rail 1317 as a plurality of segments, a more rigid material may be used for the segments whilst maintaining sufficient flexibility in the strap 1309.

To assist with assembly of the slide member 219 on to the rail 217, the strap assembly may comprise a lead-in portion 227 at one end of the rail. This lead-in portion may be at the end of the rail nearest the anchoring end of the strap, or at the end of the rail at or nearest the free end 209*c* of the strap. At the lead-in portion, the rail 217 is reduced in height and/or width by way of tapering, sloping, or thinning of the rail. It is easier to place the slide member on this reduced portion of rail, which then acts to guide the slide member into engagement with the rail in the rail portion 229.

In the example of FIGS. 6(*i*) and 6(*ii*), the lead-in portion 227 is provided at the end of the rail nearest the free end 209*b* of the strap 209 and is obscured by the looped portion of the strap during use. The cord 218 of the rail 217 terminates at the lead-in portion 227 such that the rail in the lead-in portion 227 comprises a projecting folded portion of the strap fabric 228, without the cord. The amount of fabric in the fold decreases from the rail portion 229 to the end of the lead-in portion, where the projecting rail transitions to the flat strap.

This is best illustrated in the progressive cross-sectional views of the strap/rail in FIG. 7, where FIG. 7(*i*) shows the flat strap, FIGS. 7(*i*) to 7(*iv*) show the folded strap projecting to a progressively increasing height and then increasing in width (FIG. 7(*iii*)) in preparation for receipt of the cord and to allow the rail to gradually engage with the main portion of the channel. Finally, FIG. 7(*v*) shows the rail formed by the cord, with attaching web. Along the lead-in portion, the amount of strap fabric that is contained within the lead-in to the rail gradually changes. This may result in a change in the width of the strap, for example the strap in the rail portion 229 having a width less than the width of the strap adjacent the free end 209*b*. To keep the strap width constant or to narrow the strap from the lead-in region to the free end, the side edges of the strap may be folded inwards from the lead-in region towards the strap free end 209*b*, for example, as illustrated in FIG. 8, or the strap may be narrowed using weaving techniques as described further below.

At the end of the rail opposite the end having the lead-in portion, the rail may comprise a stop to limit travel of the slide member along the rail and prevent the slide member being inadvertently slid off the rail. The stop may comprise an enlarged portion of rail that is unable to pass through the channel of the slide member, a thickened or folded part of the strap or protrusion on the strap that abuts the slide member, or a simple stitch between the rail and the strap to prevent the slide member being slid off the rail.

The strap assembly 8, 108, 208 may comprise a single rail, or a plurality of rails. Referring to the orientation shown in FIG. 17, the rails may project upwards from the strap via a vertical web, or from the side via a horizontal web, or the strap may comprise a combination or upwardly projecting and horizontally projecting rails. FIG. 17 gives number of examples of alternative profiles for the strap 9 and the rail or rails 17. It will be apparent that other configurations are possible.

The rail or rails 17 may comprise a single bead, for example as provided by a length of cord or thick yarn; or one or more rails 17' may comprise a plurality of beads arranged in a row or cluster, or consist of a bundle of threads to provide a wider or thicker rail (see FIGS. 15(*i*), 15(*ii*), and 16). The rail may be produced by stitching the strap around the cord or yarn as described above, stitching the bead to the strap, or using weaving techniques to integrally weave a thicker area into the strap to form the rails.

The strap preferably is a single layered non-stretch fabric comprising a woven textile.

FIGS. 38 to 40 illustrate exemplary methods of weaving a strap with varying size threads and thread bundles in the weft direction. FIG. 38 shows a standard, uniformly woven strap, whereas FIG. 39 illustrates an example weave for a strap with thicker yarn on the edges to provide a rail or a reinforced area for abutting a rail. In some embodiments the thread material may be varied between regions to create regions on the strap having different properties. For example, stronger threads may be provided adjacent the or each rail to withstand repeated interactions between strap material and sliding member Transitions in the yarn thicknesses must be sufficiently strong for the resulting strap to withstand the tension forces during use, and daily handling or cleaning. The transitions may utilise techniques such as a dovetail join, sewing of weft threads, interlocking wefts, or applying the "weaver's knot, or other technique to provide a smooth transition between different yarns/threads. These techniques may be implemented differently if weaving is automated using an industrial/mechanised loom machine. FIG. 40 illustrates a method for incorporating thicker yarn at the strap edges along only a portion of the strap before transitioning to a narrower strap portion or being phased out, leading to a reduction in strap width. The thicker yarn may be simply cut off and held in place by the weft threads.

Common embodiments, such as those in FIGS. 17 (ii), 17(iii), 17(v) to 17(x), 41(ii), 42(ii), and 42(ii) comprise a pair of rails, with each rail being provided along or near an opposite side edge of the strap. FIGS. 9 to 16 illustrate an exemplary embodiment having two side rails. The rails 317 may be formed using the methods described above, or by otherwise providing an elongate region or protrusion that is thicker than the thickness of the strap adjacent the rail. Referring to FIG. 9, lengths of cord 318 are stitched 325 to the parallel side edges of the strap 309, but alternatively they may be welded or otherwise attached.

Different material properties between the cords 318 and the fabric of the strap 309 may cause the strap 309 to curl slightly or significantly to form a C shaped cross-section with the cords 317 moving towards each other or even into contact as illustrated in FIG. 10. Reinforcing at one or both of the ends of the rail portion may be used to maintain the C-shaped cross section, for example by sewing, stitching, or over moulding; or the strap may be heat treated to help with shape retention.

Alternatively or additionally, the properties of the strap such as differences in stiffness or thickness may be non-uniform, particularly in the weft direction of the strap to promote such curling. For example, providing thinner, more compliant regions near the side edges may encourage curving of the strap in those regions and also reduce the tendency for the strap to uncurl distal to the slide member. Further, the weave of the strap may be selected to maximise curling of the strap, for example, weft-knitted fabrics can tend to curl inwards due to the torque of the woven yarn, particularly if the edges are cut.

In embodiments having two rails, the slide member has two channels to receive the respective two rails. FIG. 11 shows an exemplary slide member 319 with left and right side-opening channels 321. The channels 321 are defined between top and bottom walls of the slide member and separated by channel dividers 333. Each channel 321 has a cross-sectional profile suitable to receive a respective cord 318, and an opening for the strap 316 adjoining the cord 317 to pass through. In the embodiment shown, the channel openings are at the side of the slide member in the form of a slot 331 for use with the strap of FIGS. 9 and 10, The width of the slot 331 is the same as or larger than the thickness of the strap adjacent the cord, and less than the diameter of the cord 318.

As shown in FIGS. 13(i) to (iv), when the rails are positioned within the channels, the strap 309 extends through one side slot 331, around the under surface of the slide member 319, and through the opposing side slot 331. That is, the strap 309 wraps closely under the slide member 319 such that the strap contacts the under surface of the slide member, optionally laterally tensioning the strap. The top surface of the slide member remains exposed, for attachment to the free end of the strap. More lateral tension in the strap will result in increased friction forces between the slide member under surface and the strap. This friction must be overcome to adjust the slider along the rails, but sufficient friction forces resist the forces acting on the strap and slide due to gas flow into the interface during use, thereby passively maintaining the position of the slide member preventing movement of the slide along the rail.

Referring again to FIGS. 11(i) to (iv), the channels 321 are defined between the slide member's top and bottom walls 320a, 320b, and lateral walls 332, and by one or more central spacers 330. The embodiment shown comprises two spacers 330, with gap between the spacers. The gap between the two spacers 330 forms a passage bridging the two channels. In alternative embodiments, the two channels may be defined by a single spacer, with no passage bridging the channels.

Each channel 321 has a lead-in region 335 at its leading and trailing ends where the channel widens. This widened lead-in region acts as a guide to direct the rail into the channel 321 and may gradually apply lateral tension to the strap by pulling the rails inwards, for smoother movement of the slide member 319 along the rail. The lead-in channel region may also or alternatively assist with initial assembly of the slide member onto the rail.

The widened region may be created by one or more walls of the channel tapering outwards from the channel, for example to create a fluted shape. In the embodiment of FIG. 11, the lateral wall 332 of each channel 321 tapers laterally outwards at the leading and trailing ends of the channel. In addition, each edge of the channel opening at the leading and trailing ends is filleted 334 to further enlarge the entrances to the channels and guide the slide member onto and smoothly along the rail.

In the embodiment of FIGS. 12 to 14 the curved strap has a width that is substantially the same, or only slightly larger than the width of the slide member. In alternative embodiments, the slide member may have a width that is less than the width of the strap, for example 40 to 60% of the width of the strap. For example, in the embodiments of FIGS. 17(x) and 18, the sides of the strap are folded inwards and stitched (or otherwise fastened) in the folded position such that the spacing between the two side rails 417 is much less than the spacing between the sides of the strap member. This embodiment reduces the tendency for the edges of the strap to uncurl and pull the rail outwards in the channels, reducing friction and making sliding of the slide member along the rails easier. It also reduces lateral tension forces on the skin-contacting portion of the strap, enabling the use of softer, more comfortable strap materials that may not be able to withstand tension forces. Finally, it may allow for a smaller, more discrete slide member and a larger strap area contacting the wearer (which may provide more stability or comfort).

In some embodiments, the channels 521 defined in the slide member 519 may be non-linear, for example, curved, angled, or otherwise shaped. The shaping of the channels forces the rail 517 along a tortuous path as the slide member 519 moves along the strap 509, thereby increasing the friction forces between the rail 517 and the inner surfaces of the channel 521 compared with a straight channel. These increased friction forces act to oppose movement of the slide along the rail, thereby increasing the ability of the strap assembly to resist forces acting on the strap assembly due to gas flow into the interface during use, thereby passively maintaining the position of the slide member preventing movement of the slide along the rail.

FIGS. 19 to 22 show one such embodiment having a slide member 519 with curved channels 521. In this embodiment, the curved channels are defined by the shape of the lateral walls of the channel 532 and the spacer members 533. Referring to FIG. 20 and the section view of FIG. 21, the two channels 521 are oppositely curved such that the spacing between the channels varies along the slider 519, with the channels being closest together at their longitudinal midpoints and most spaced at their leading/trailing ends. The channels 521 thereby alter the spacing between the rails 517 as the slider moves along the strap, the slide member 519 pinching the rails 517 towards each other as it is moved along the strap 509.

As well as increasing friction forces acting between the internal channel surfaces and the rail, in embodiments where the strap wraps closely around the slide member 519, the act of pinching the rails towards each other also pulls the strap closer into contact with the under surface and side surfaces of the slide member 519, and may tension the strap in its transverse direction, increasing resistance to movement of the slide member.

In alternative embodiments, the slide member may comprise an adjustable mechanical lock mechanism for selectively increasing or reducing the friction between the rail and the slide member and/or selectively locking or unlocking the slide member to the rail(s). The lock mechanism is adjustable between an unlocked configuration for allowing movement of the slide member along the rail, and a locked configuration for resisting or preventing movement of the slide member along the rail by compressing the rail or creating a tortuous path. When in the locked configuration, the lock mechanism presses the rail or rails into a wall of the channel, and may compress the rail, to prevent free movement of the slide along the rail.

The lock mechanism may be manually adjusted between the locked configuration and the unlocked configuration, may be toggled between the locked configuration and the unlocked configuration using a toggle mechanism, or may be automatically moved from one configuration towards the other upon loading of the straps.

FIGS. 23 to 27(*ii*) illustrate one embodiment lock mechanism having a rotatable cam. Referring to FIGS. 23 and 24, the slide member 632 that houses the lock mechanism comprises a cylindrical aperture 643 to receive a lock component 641. The aperture 643 extends through both of the channels in the slide member 619.

The lock component 641 has a complementary cylindrical base 646a and cylindrical top 646b to act as a bearing surfaces, rotatably bearing against the walls of the aperture in the top and bottom walls of the slide member 619. Therefore, the lock component 641 is rotatable relative to the slide member 619. A mid portion of the lock member 641 comprises a cam 647 that is aligned with the channels 621 as illustrated in FIG. 27(*ii*).

The cam 645 has a shape having major dimension along a major axis and a minor dimension along a minor axis, the minor dimension being shorter than the major dimension. In one embodiment the cam is elliptical and the minor dimension is less than about 60% of the length of the major dimension. In the unlocked configuration of the mechanism, shown in FIGS. 26(*i*) and (*ii*), the cam is rotated to an unlocking position such that its major axis is substantially parallel to the longitudinal direction of the rails, slide member and strap. The minor dimension of the cam is approximately the same as or less than the spacing between the two channels 631 such that in the unlocking position, the cam 646 does not protrude into the channels, or protrudes only slightly, so to not occlude the channel or not inhibit the free passage of the rails along the channels.

In the locked configuration of the mechanism, shown in FIGS. 27(*i*) and (*ii*), the cam 645 is moved to a locking position by rotating the lock member 641 through about 90 degrees. In the locking position the minor axis is substantially parallel to the longitudinal direction of the rails, and the major axis is substantially perpendicular to the longitudinal direction of the rails such that the cam 646 protrudes into the channels, to create a narrowing in the channels. The rails 617 are compressed by the cam surface 647 against the lateral sides of the respective channel, as illustrated in FIG. 27(*ii*) to lock the position of the slide member 619 relative to the rails. The major dimension of the cam 645 is less than the distance between the facing lateral sides of the channels 621 such that there is a gap 649 between the cam surface 647 and the lateral sides in which the compressed rail can fit. Each gap 649 is smaller than the diameter of the respective rail such that the rail 617 must be compressed to fit through the gap.

In this embodiment, the aperture 643 extends through the top and bottom portions of the slide member to enable rotatable mounting of the locking member 641 relative to the slide member 619. Top and bottom lips 648a, 648b locate the locking member vertically relative to the housing and prevent movement of the locking member along the axis of rotation during use. However, it will be appreciated that other arrangements are possible, for example the rotatable lock component may sitting in a circular recess or be rotatably attached to the slide member via an axle. A handle such as a knob or other grip (not shown) preferably protrudes from the locking member to facilitate rotation of the cam.

Rather than rotating, the lock component may slide relative to the slide member. FIGS. 28(*i*) to 30(*iii*) illustrate alternative embodiment slide members having a sliding type locking mechanism. These embodiments comprise a sliding block 741, 841 housed within the slide member 719, 819, the block being slidable longitudinally between an unlocking position and a locking position. In the locking position, a surface of the block presses each rail into a channel wall to compress the rail and prevent movement of the slide member along the rail. In the unlocking position, the block allows free passage of the slide member 709, 819 along the strap.

The block 741, 841 comprises at least two rail contacting surfaces 747, 847, preferably provided on the sides of the block. The rail contacting surfaces 747, 847 and the facing surfaces of the channels 732, 832 are not parallel with the longitudinal direction, therefore, movement of the block 741, 841 in the longitudinal direction moves the two rail contacting surfaces towards or away from the facing surfaces of the channels 732, 832.

In the embodiment of FIG. 28, the block 741 comprises opposite convex side surfaces 747 and the slide member comprises corresponding facing concave surfaces 732. The convex side surfaces 747 of the block and the interior concave surfaces 732 of the slide member together define the channels 721 for the rails. It will be appreciated that rather than being curved, the convex/concave surfaces may instead taper linearly from the widest mid-point.

The block 741 has end cut-outs 750 to locate the block and guide its movement within the slide member housing 741. The slide member 719 has two centrally positioned end stops 751 provided at the leading and trailing ends of the slide member 719. When positioned within the slide member, the cut-outs in the block receive the end stops 751. The width of the end stops 751 slightly less than the width of the cut-outs 750 such that the end stops fit closely in the cut-outs to minimise any transverse movement of the block relative to the slide member 719 while still permitting easy sliding of the block.

The spacing between the two end stops 751 is less than the overall length L of the slide member 719 so that the block remains engaged throughout its movement, but the end stop spacing is greater than the distance between the end cut-outs 750 thereby creating gaps M1, M2 between each cut-out and the respective end stop to allow longitudinal movement of the block 741.

The block is in its unlocking position when it is positioned centrally in the fore-aft direction as shown in FIG. 28(i), where the spacing M1 is substantially the same as M2, and width of each channel 721 is substantially the same along the length of the block. To move the locking mechanism into the locking configuration, the block 741 is moved towards a locking position at the leading or trailing end of the slide member 719, increasing one of M1 or M2 while minimising the other one of M1 or M2, and thereby narrowing the channels at one end of the channels. The movement of the block 741 pushes the rail into the convex channel wall at the narrowed end, compressing the rails, to prevent free passage of the slide member 719 along the rails.

The locking mechanism may comprise a handle such as a protruding knob or other grip to facilitate movement of the block (not shown). The mechanism may further comprise fixing means to secure the block in either the locked or unlocked position to prevent inadvertent movement of the block 741.

FIGS. 29(i) to 30 illustrate a further embodiment locking mechanism comprising a longitudinally sliding block 841 that is asymmetric in a forward-rearward direction of the block. The block 841 tapers general from a front end to its rear end, with its side surfaces 847 being oppositely angled. The slide member comprises corresponding facing angled surfaces 832. The angled side surfaces 847 of the block and the facing angled surfaces 832 of the slide member together define the channels 821 for the rails 817.

The angled surfaces 847 of the block have a transverse dimension towards one end of the block 841 that is greater than the transverse dimension near the other end of the block. The block 841 has end cut-outs 850 to locate the block and guide its movement within the slide member housing 841 in the manner described above in relation to the embodiment of FIG. 28.

FIG. 29(iii) illustrates the lock mechanism in its unlocking configuration in which the width of each channel 821 is substantially the same along the length of the block and the slide member 819 is able to move freely along the rail. FIG. 29(iv) illustrates the block 841 moved into the locking position by sliding the block longitudinally to narrowing the channels between the angled side 847 of the block and the angled surface 832 of the slide member 832. The movement of the block 841 pushes the rail into the angled channel wall, compressing the rails, and thereby preventing free passage of the slide member 819 along the rails 817.

The lock mechanism is oriented such that when the strap assembly is in tension, such as during use of a respiratory interface, the forces acting on the slide block and slide member 832 urge the lock mechanism towards its locking configuration to automatically lock the strap assembly and prevent or minimise any change in the length of the strap due to the tension. The strap free end may attach to the slide member 819, so the strap tension pulls the slide member in the direction of the strap loop portion and the block 841 is held substantially in place by friction forces between the strap and the block. Alternatively (as illustrated in FIG. 30), the strap free end may attach directly to the slide block 841, so the strap tension pulls the slide block 841 in toward the strap loop portion while the slide member 819 is held substantially in place by friction forces between the slide member 819 and strap 816.

For the embodiment of FIGS. 29 and 30, the slide block 841 has a handle 853 that projects through a slot in the upper portion of the slide member 819. The strap free end 809 attaches to that handle 853. In addition, the block 841 can be moved between its unlocking position and its locking position by sliding the handle along the slot. The slide member is oriented with the narrow end of the slide block most proximal the loop portion of the strap and the wide end most proximal the anchoring end of the strap.

In an embodiment with the strap free end 809 attached to the slide member 819 rather than the slide block, the slide block 841 and slide member would be arranged such that the wide end of the slide block is most proximal the loop portion of the strap and the narrow end is most proximal the anchoring end of the strap.

Yet further embodiment lock mechanisms 941, 1041 are illustrated in FIGS. 31 to 37. In these embodiments, the lock mechanism comprises a rocking lock member 941, 1041 that is pivotably mounted to the slide member at about a transverse pivot 957, 1057. The rocking member is pivotable between an upright unlocking position as shown in FIG. 33, and a tilted locking position shown in FIG. 35.

The rocking member comprises a body 952 and a base portion 947. The pivot 957 extends through the body 952, with the portion of the body above the pivot forming the handle 953. The handle 953 protrudes beyond the top surface of the slide member 916 to provide purchase for the user's fingers. As is illustrated in FIG. 34, the body 952 is positioned between the two channels in the slide member 919, but the base member extends across the width of the two channels 921. In the upright unlocking position, the top surface of the base portion 947 is substantially flush with the bottom of the two channels so as to not inhibit free passage of the rails through the channels.

To move the rocking lock member 941 into the locking position, the rocking member 941 is tilted about the pivot 957 to one side to cause the base portion 947 to project up into the channel 921, thereby compressing the rails (not shown) by pressing them into the top surface of the channel to prevent movement of the slide member 919 along the strap. Optionally the base portion 1047 may comprise teeth 1059, as shown in the embodiment of FIGS. 36 and 37, to grip the rails.

The under surface of the base member 947, 1047 is convex, preferably having a radius of curvature equivalent to the distance between the base under surface and the pivot 957, and centred on the pivot axis 957, to provide clearance between the base 947 of the lock member and the slide member housing as the rock member 941 is rotated about the pivot axis.

Referring to FIG. 37, the free end of the strap 1009b is attached to the handle 1053 of the rocking member 1041. When the assembled headgear strap 1009 is looped around a post 1003 and the mask is in use, the strap 1009, including the looped portion, is tensioned. The tension urges the rocking member 1053 towards a tilted orientation relative to the slide member 1016, with the handle 1053 tilting towards the post 1003. Thereby urging the teeth 1059 on the side of the rocking member base 1047 most distal to the post 1003 into engagement with the rails 1017. Therefore, when the mask is worn by the user, the strap tension holds the locking mechanism in the locked configuration with the rails 1017 engaged/compressed by the teeth 1059. This opposes the blow-off forces during CPAP therapy to keep the mask stable on the user's face.

For all of the above described embodiments, the strap 9 folds over on itself and attaches to the slide member 19 at or near the free end 9b of the strap 9 forming a looped portion of strap. Moving the slide member along the rail changes the length of the loop portion, thereby changing the length of the strap assembly 8.

Typically the strap attaches to the top surface of the slide member 19, but other attachment points on the slide member 19 are possible. For example, the strap may attach to the locking mechanism handle (as shown in FIG. 32), or an anchor point on another part of the slide member. The attachment between the strap and the slide member may be either permanent, for example using an adhesive or overmoulding, or removable, for example using a hook-and-eye type fastener, a dome-type hole and stud, or button attachment. A removable attachment provides the advantage of easily disassembly of the strap assembly from the respiratory interface for cleaning. Alternatively, the attachment between the strap and the slide member may be indirect via a third component that attaches to each or the strap and the slide member.

To assemble the head gear on the respiratory interface, the strap may first need to be passed through the eye of an anchor point, for example through an aperture such as a slot or D-shaped connector 3 provided on the respiratory interface as shown in FIG. 2, before attaching the free end of the strap end to the slide member 17. Alternatively the strap may be wrapped around a post on the frame of the respiratory interface. In other embodiments, the looped portion of the strap may be attached to a separate connector, for example threaded through an aperture such as a slot in the connector. The connector is then removably engageable with the respiratory interface to allow for easily removal of the headgear from the frame, for example, the connector may have a clip for hooking to a post on the frame of the respiratory interface.

Referring back to FIG. 2, the headgear is configured such that the two strap assemblies lie along the sides of a wearer's face. For comfort and ease of adjustability, the strap assembly is arranged such that a flat under surface of the strap contacts the user's face, with the rail, slide member and the free end of the strap sitting over this portion of the strap. The wearer can readily adjust the fit of the headgear by grasping the slide members at the sides of their head, and moving the slide members forwards or backwards along the strap to shorten or lengthen the strap assembly. The frictional nature of the attachment of the slide member to the strap allows for continuous fine adjustment of the position of the slide member on the rail.

For comfort, softer or wicking fabric may be utilised on the skin-contacting region of the strap. For example, a low density satin-like material formed using a plain, twill, or satin weave; or through the use of thread piles. The strap fabric may utilise any suitable yarn material or combination of materials such as but not limited to natural plant-based fibres, animal-based fibres, or synthetic fibres, depending on the desired characteristics for the strap.

The other components of the strap assembly comprise any suitable material as will be apparent to a skilled person. For example the slide member may comprise a plastic material such as rigid Nylon. However, it will be apparent to those skilled in the art that other rigid materials such as other plastics, composite materials, or metals may be substituted without departing from the scope of the invention.

Preferred embodiments of the invention have been described by way of example only and modifications may be made thereto without departing from the scope of the invention.

What is claimed is:

1. A headgear for a respiratory interface having a strap assembly comprising:
    an elongate flexible strap;
    a rail or a pair of rails extending longitudinally along a rail portion of the strap, and a slide member having a channel that receives the rail or a pair of channels each of which receives a respective one rail of the pair of rails;
    wherein the slide member is attached to an attachment portion of the flexible strap and slidable along the rail or the pair of rails to adjust the length of the strap assembly;
    wherein the strap comprises woven threads of different thicknesses, or woven bundles of varying numbers of threads, to vary the width or thickness of the strap.

2. The headgear of claim 1, wherein the slide member is fixedly attached to the attachment portion of the flexible strap.

3. The headgear of claim 1, wherein the slide member is fixedly attached to the flexible strap at or near a free end of the strap.

4. The headgear of claim 1, wherein the rail connects to the strap via an adjoining web.

5. The headgear of claim 1, wherein the rail substantially aligns with a centre line of the strap rail portion.

6. The headgear of claim 1, wherein each rail of the pair of rails is provided along an opposite side edge of the strap.

7. The headgear of claim 6, wherein the rail portion of the strap forms a C-shape cross section, at least in a region adjacent the slide member.

8. The headgear of claim 1, wherein the rail or each rail of the pair of rails has a width that is greater than a thickness of the strap or web adjoining the rail.

9. The headgear of claim 1, wherein the channel or each channel of the pair of channels has a profile comprising a main recess that receives the rail or one rail of the pair of rails and a necked opening to receive the strap or a web extending between the rail or the one rail of the pair of rails and the strap, wherein the opening is narrower in width than the main recess.

10. The headgear of claim 1, wherein the properties of the strap are non-uniform.

11. The headgear of claim 1, wherein the strap comprises woven threads of different materials to create regions on the strap having different properties.

12. The headgear of claim 1, wherein stronger threads are provided adjacent the rail or each rail of the pair of rails.

13. The headgear of claim 1, wherein softer or wicking threads are provided on a skin-contacting region of the strap for comfort.

14. The headgear of claim 1, wherein woven threads of greater thickness or woven bundles of greater number of threads provide the rail or each rail of the pair of rails or a reinforced area for abutting the rail or each rail of the pair of rails.

15. The headgear of claim 1, wherein the woven threads are woven in a weft direction.

* * * * *